US007618782B1

(12) United States Patent
Van Eyk et al.

(10) Patent No.: US 7,618,782 B1
(45) Date of Patent: *Nov. 17, 2009

(54) METHODS OF DIAGNOSING MUSCLE DAMAGE

(75) Inventors: Jennifer E. Van Eyk, Kingston (CA); Ralf Labugger, Zurich (CH); Irena Neverova, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/419,901

(22) Filed: Oct. 18, 1999

(51) Int. Cl.
  *G01N 33/53* (2006.01)
  *G01N 33/543* (2006.01)

(52) U.S. Cl. ............... 435/7.1; 435/7.21; 435/7.92; 436/518; 530/300; 530/350

(58) Field of Classification Search .......... 435/15, 435/194, 7.1, 7.21, 7.92; 424/906, 94.1; 530/841, 300, 350; 436/518

See application file for complete search history.

(56) References Cited

U.S. PATENT DOCUMENTS

| 5,290,678 A | 3/1994 | Jackowski .............. 435/7.4 |
| 5,834,220 A * | 11/1998 | Wicks et al. ............ 435/7.92 |
| 6,248,549 B1 * | 6/2001 | Van Eyk et al. .......... 435/15 |
| 2002/0072590 A1 | 6/2002 | Van Eyk et al. |
| 2004/0072255 A1 | 4/2004 | Van Eyk et al. |

FOREIGN PATENT DOCUMENTS

| CA | 2243372 | 7/1998 |
| WO | WO 94/27156 | * 11/1994 |
| WO | WO 96/10076 | 4/1996 |
| WO | WO 96/10078 | * 4/1996 |
| WO | WO 96/33415 | 10/1996 |

OTHER PUBLICATIONS

Bodor et al. Circulation, vol. 96, No. 5, Sep. 2, 1997, pp. 1495-1500.*
Thompson et al. (Cell. Signal. vol. 10, No. 1, pp. 1-11, 1998).*
Chan et al. (Biosensors and Bioelectronics, 20, 2005m 2566-2580).*
Solaro et al. (Journal of Molecular Cell Cardiology, vol. 28, pp. 217-230, 1996).*
Lin et al. (The journal of Biological Chemistry, vol. 271, No. 1, Jan. 5, 1996, pp. 244-249).*
Han et al. (International Journal of Biochemistry, vol. 24, No. 1, 1992, pp. 19-28).*
Jideama et al. (The Journal of Biological Chemistry, vol. 271, No. 38, Sep. 20, 1996, pp. 23277-23283).*
Lofberg et al. (Archives of Neurology, vol. 52, Dec. 1995, pp. 1210-1214).*
Andres, J., et al., Contractile proteins in globally "stunned" rabbit myocardium. Basic Res. Cardiol., 86:219-226 (1991).
Bartel, S., et al., Protein phosphorylation in islolated trabeculae from nonfailing human hearts. (Abstract) Mol. Cell Biochem., 157:171-179 (1996), abstract only.
Bodor, G. S., et al., Troponin I phosphorylation in the normal and failing adult human heart. Circulation, 96:1495-1500 (1997).
Jideama, N.M., et al., Phosphorylation specificites of protein kinase C isozymes for bovine cardiac troponin I and troponin T and sites within these proteins and regulation of myofilament properties. J. Biol. Chem., 271:23277-23283 (1996).
Kaumann, A., et al., Activation of $\beta_2$-adrenergic receptors hastens relaxation and mediates phosphorylation of phospholamban, troponin I, and C-protein in ventricular myocardium from patents with terminal heart failure. Circulation, 99:65-72 (1999), Jan. 5/12.
Matejovicova, M., et al., Phosphorylation by protein kinases A and C of myofibrillar proteins in rabbit stunned and non-stunned myocardium. J. Mol. Cell Cardiol., 29:3189-3202 (1997).
McConnell, B.K., et al., Troponin I phosphorylation and myofilament calcium sensitivity during decompensated cardiac hypertrophy. Amer. J. Physiol.—Heart and Circulatory Physiology, 274:H385-H396 (1998).
McDonough, J.L., et al., Troponin I degradation and covalent complex formation accompanies myocardial ischemia/reperfusion injury. Circ. Res., 84:9-20 (1999).
Wolf, M.R., et al., Myofibrillar calcium sensitivity of isometric tension is increased in human dilated cardiomyopathies. J. Clin. Invest., 98:167-176 (1996).
Yuasa, K., et al., A novel interaction of cGMP-dependent protein kinase I with troponin T. J. Biol. Chem., 274:37429-37434 (1999).
U.S. Appl. No. 09/115,589, filed Jul. 15, 1998, Van Eyk et al.
Collinson, P.O., et al., Measurement of Cardiac Troponins. *Ann. Clin. Biochem.* 38(Pt 5): 423-449 (2001).
Hartner, K., Pette, D., Fast and Slow Isoforms of Troponin I and Troponin C. Distribution in Normal Rabbit Muscles and Effects of Chronic Stimulation. *Eur. J. Biochem.* 188: 261-267 (1990).
Konagaya, M., et al., Increased Serum Myosin Light Chain 3 Level in Neuromuscular Diseases. *Muscle & Nerve* 10(5): 415-421 (1987).
Larue, C., et al., Immunoradiometric Assay of Myosin Heavy Chain Fragments in Plasma for Investigation of Myocardial Infarction. *Clin. Chem.* 37(1):78-82 (1991).
Morano, I. et al., Phosphorylation and Thiophosphorylation by Myosin Light Chain Kinase: Different Effects on Mechanical Properties of Chemically Skinned Ventricular Fibers from the Pig. *J. Mol. Cell Cardiol.* 22: 805-813 (1990).
Ravkilde, J., Creatine Kinase Isoenzyme MB Mass, Cardiac Troponin T, and Myosin Light Chain Isotype 1 as Serological Markers of Myocardial Injury and their Prognostic Importance in Acute Coronary Syndrome. *Dan. Med. Bull.* 45 (1): 34-50 (1998).
Takahashi, M., et al., Use of Enzyme Immunoassay for Measurement of Skeletal Troponin-I Utilizing Isoform-Specific Monoclonal Antibodies. *Clin. Biochem.* 29 (4): 301-308 (1996).
U.S. Appl. No. 11/138,184, filed May 26, 2005, Eyk and Simpson.
Westfall et al., "Alterations in Myofibrillar Function and Protein Profiles After Complete Global Ischemia in Rat Hearts", Circulation Research 1992 70:302-313.
Van Eyk et al., "Cardiac Disease-Induced Post-Translational Modifications of Troponin I:Differential Proteolysis, Phosphorylation and Covalent complex formation", Biophysical J. 2001 80(5) 44th Annual Meeting of the Biophysical Society, Feb. 12-16, 2000 632-POS XP008028766.

* cited by examiner

*Primary Examiner*—Lisa V Cook
(74) *Attorney, Agent, or Firm*—Licata & Tyrrell P.C.

(57) ABSTRACT

A method for assessing muscle damage in a biological sample obtained from a subject is disclosed. The method involves obtaining a biological sample from a subject being assessed for muscle damage, and evaluating the sample for the presence or absence of a myofilament protein modification product. Preferably, the myofilament protein modification product is a chemical adduct of a myofilament protein. The method can also be used to assess the extent and/or type of muscle damage in a subject by studying the profile of myofilament protein modification products detected in the sample taken from the subject. The invention further provides a method for screening for an agent which modulates the level of a myofilament protein modification product an present in a biological sample or for a calcium sensitizing agent. The invention is applicable to cardiac muscle and skeletal muscle.

26 Claims, 14 Drawing Sheets

METHODS OF DIAGNOSING MUSCLE DAMAGE

FIELD OF THE INVENTION

This invention relates to methods for diagnosing cellular damage of skeletal and cardiac muscle.

BACKGROUND OF THE INVENTION

When circulation of blood, and therefore oxygen, to muscle is interrupted (ischemia and/or hypoxia), the ability of the muscle to contract is impaired. Even if circulation is restored (e.g., by reperfusion), muscle function can remain depressed. In cardiac muscle, the effects of ischemia can have severe consequences, and inadequate circulation of blood to the heart is one of the most important causes of morbidity in developed countries. Clinically, ischemia and reperfusion injury manifest as a spectrum. In its mildest form, ischemia is transient, reperfusion is established quickly and the reduced contractility of the muscle tissue is temporary and reversible. However, longer and more severe ischemia produces irreversible damage and cellular necrosis.

Myofilament specific proteins, such as troponin I (TnI), troponin T (TnT), and troponin C (TnC) (members of the regulatory complex), myosin light chain 1 (MLC1), and $\alpha$-actinin are modified during hypoxemia (i.e., reduced delivery of oxygen due to a reduced partial pressure and/or arterial content of oxygen), ischemia, and/or ischemia/reperfusion injury. Modification of these proteins affects muscle contraction by apparently altering interactions of TnI, TnT, TnC, myosin light chain 1, and $\alpha$-actinin with other proteins critical for normal muscle contraction.

Specific and selective modification of cardiac TnI (cTnI) has been proposed as the molecular mechanism that underlies the contractile dysfunction observed in stunning, and other mild reversible forms of ischemia/reperfusion injury (Bolli et al. 1999, *Phys. Reviews* 79:609-634; McDonough et al. 1999, *Circ. Res.* 84:9-20; Van Eyk et al. 1998, *Circ. Res.* 82:261-271; Foster et al. 1999, *Circ. Res.* 85:470-472; Solaro et al. 1999, *Circ. Res.* 84.122-124). Accordingly, detection and quantification of cTnI in serum of patients suffering from acute coronary syndromes has become the most specific and sensitive biochemical marker available for myocardial injury, due to necrotic release of the cardiac-specific isoform. Until recently the standard diagnostic tools for detecting myocardial damage were measurements of the serum CKMB enzyme (creatine kinase muscle brain isoform) and the ECG (electrocardiogram). Evidence indicates that troponin should supplement or even replace CKMB not only for reasons of diagnostic superiority, but also for its prognostic power (Hamm et al. 1998, *N. Engl. J. Med.* 337:1648-53). However, routine use of cTnI detection as a clinical diagnostic tool has been hampered by up to 20-fold quantification discrepancies among commercially available detection kits, which discrepancies are thought to be due to the presence of modified cTnI in serum (Wu et al. 1998, *Clin. Chem.* 44:1198-1208; Christenson et al. 1998, *Clin. Chem.* 44:52-60). In vitro isolated perfused rat heart models have demonstrated that the principle components of the reperfusion effluent are cTnI modification products, including degradation products and protein-protein complexes (McDonough et al. 1999, *Circ. Res.* 84:9-20; Van Eyk et al. 1998, *Circ. Res.* 82:261-271). In support of this, Wu et al. (1998, *Clin. Chem.* 44:1198-1208) purified the troponin I products from the serum of myocardial infarction patients, and demonstrated the presence of complexes between cTnI/cTnC, cTnI/TnC/TnT, and little if any intact cTnI (Wu et al. 1998, *Clin. Chem.* 44:1198-1208). Together, these results suggest that modified troponin products are preferentially released from dying/dead cardiomyocytes. Also, in vitro studies with recombinant cTnI have demonstrated that blood can modify cTnI, producing cTnI degradation products (Shi et al. 1999, *Clin. Chem.* 45:1018-1025; Katrukha et al. 1998; *Clin. Chem.* 44:2433-2440). Despite this knowledge, all commercially available detection kits continue to be standardized against some form of exogenous cTnI (including recombinant expressed cTnI and synthetic cTnI peptides; Shi et al. 1999, *Clin. Chem.* 45:1018-1025). Similarly, the presence of cTnT or MLC in serum is a biochemical marker for myocardial damage (Ravkilde 1998, *Dan. Med. Bull.* 45:34-50); however, specificity issues arise when using commercially available detection kits because of the lack of appropriate cardiac-specific isoforms of these proteins. The inability to detect and quantify modified myofilament proteins in serum is a significant barrier to the development of reliable diagnostic and therapeutic methods for ischemic muscle damage.

SUMMARY OF THE INVENTION

The present invention provides methods for assessing cardiac and skeletal muscle damage in a subject. The method includes obtaining a biological sample from a subject being assessed for muscle damage and evaluating the sample for presence or absence of one or more myofilament protein modification products, at least one of the myofilament protein modification products being a chemical adduct of a myofilament protein, and other modification products including, for example, individual protein fragments, or protein-protein complexes formed from two or more myofilament proteins, which may be intact proteins or protein fragments in the biological sample, wherein the presence of at least one myofilament protein modification product in the biological sample is indicative of muscle damage in the subject.

According to a preferred embodiment of the invention, there is provided a method for assessing muscle damage in a subject, comprising: obtaining at least two biological samples from a subject being assessed for muscle damage; and evaluating for the presence or absence of one or more myofilament protein modification products in the biological samples; wherein the biological samples are not obtained simultaneously; and wherein the presence of one or more myofilament protein modification products in at least one of the biological samples is indicative of muscle damage in the subject. Preferably, at least one of the myofilament protein modification products is a chemical adduct of a myofilament protein. In another preferred embodiment, the method includes assessing a change with time in the presence or amount of one or more myofilament protein modification products in the biological samples, as an indication of the extent of muscle damage in the subject.

According to one aspect of the invention, the presence and amount of myofilament protein modification product present in a biological sample can be assessed as an indication of the extent of muscle damage in the subject. In accordance with the invention, a method of assessing muscle damage in a subject comprises obtaining a biological sample from a subject, incubating the biological sample with at least one compound which specifically binds to one or more different myofilament proteins or myofilament protein modification products present in the sample, at least one of the myofilament protein modification products being a chemical adduct of a myofilament protein, under conditions which allow the compound to form one or more complexes with the myofilament proteins or myofilament protein modification products, detecting said one or more complexes, and characterizing the profile of said one or more myofilament proteins or myofilament protein modification products contained in said one or more complexes, as an indication of the extent or type of muscle damage in the subject. The compound can for example be an antibody, a protein, a peptide or a peptidomimetic that forms a complex with the myofilament protein modification product. In certain embodiments, the myofilament protein is troponin I, troponin T, troponin C, myosin light chain 1, α-actinin or a fragment(s) or combination(s) thereof.

The invention also provides a kit for assessing myocardial damage in a biological sample obtained from a subject. In one embodiment, the kit includes a compound which specifically binds to a chemical adduct of a myofilament protein and instructions explaining how to use the kit to assess muscle damage in a biological sample obtained from a subject. In other embodiments the compound may bind to one or more myofilament protein modification products, at least one of the myofilament protein modification products being a chemical adduct of a myofilament protein. The kit may also include a label or labelled compound used to identify the myofilament protein modification product(s) thereof. The kit may further include a reagent(s) appropriate for detecting the label.

The invention further provides assays, e.g., screening tests, for identifying an agent which modulates the level of one or more myofilament protein modification products in a biological sample, at least one of the myofilament protein modification products being a chemical adduct of a myofilament protein. The assay involves obtaining a biological sample containing a myofilament protein modification product from a subject, testing the biological sample with an agent (e.g., contacting the sample with the agent), and determining the effect of the agent on the level of the myofilament protein modification product in the biological sample, wherein an agent(s) which modulates the level of the myofilament protein modification product in a biological sample is identified.

In accordance with the invention, the presence and level of myofilament modification products in a biological sample are detected, at least one of the myofilament protein modification products being a chemical adduct of a myofilament protein. The biological sample can be obtained from any subject exhibiting, exposed to, suspected of having, or being treated for, a condition or conditions which could cause hypoxemic/ischemic damage to muscle tissue. The invention therefore also provides for the assessment of efficacy of, for example, treatments such as cardioplegia (preservation) and preconditioning of the myocardium, and rehabilitation following heart disease-related injury such as infarction. The invention is also applicable to rehabilitation of patients with skeletal muscle damage, disease such as rhabdomyolysis, respiratory diseases such as, but not restricted to, chronic obstructive pulmonary disease, emphysema, asthma and bronchitis, bullectomy (lung reduction surgery), and following insult due to surgery or other trauma. The invention further provides for the assessment of the appropriateness of the level of training in athletes and animals such as race horses, where myofilament modification products as indicators of skeletal muscle breakdown can be detected. Yet other applications of the invention include the diagnosis of respiratory muscle dysfunction, wherein myofilament modification products can also exist.

Other features and advantages of the invention will be apparent from the following detailed description, and from the claims.

BRIEF DESCRIPTION OF THE DRAWINGS

Embodiments of the invention will now be described, by way of example, with reference to the accompanying drawings, wherein:

FIG. 9A shows the timecourse of CKMB and cTnI release for the two groups, Group 1 (solid circles) and Group 2 (open circles).

FIG. 9B shows an anti-TnI antibody (8I-7) western blot of the 12.5% SDS-PAGE separated serum timecourse, and the serum cTnI measurements using the detection kit.

FIG. 9C shows the amount of each of the principle cTnI modification products present in the myocardium of patients in the two serum groups before application of the cross-clamp, expressed as the % of total TnI in the sample (open bars, Group 1; filled bars Group 2). Values are mean±standard error, and significant differences * are p<0.05.

FIG. 10A shows anti-cTnI antibody (8I-7) western blots of 12.5% SDS-PAGE with 3 mol/L urea separated left ventricle tissue samples from two patients who fall into Group A and Group D with respect to Deg 1. Deg 1 is present both before and after cross-clamp in patient 1 (therefore Group A), but never present in patient 2 (therefore Group D).

FIG. 10B shows the timecourses of CKMB and cTnI release for patients in Group A (filled circles) and Group D (open circles) with respect to Deg 1.

FIG. 10C shows the quantity of each degradation product present in the myocardium of patients in each group, before (open bars) and after (hatched bars) the cross-clamp. Note that Group D patients are by definition valued at 0 (i.e. never present) and are not shown. Values are given as mean±standard error, and significant differences are given as +different from 0 (including Group B before cross-clamp, Group C after cross-clamp, and Group D) p<0.05, and * different between before and after cross-clamp within each group p<0.05.

DETAILED DESCRIPTION

Figure 1:
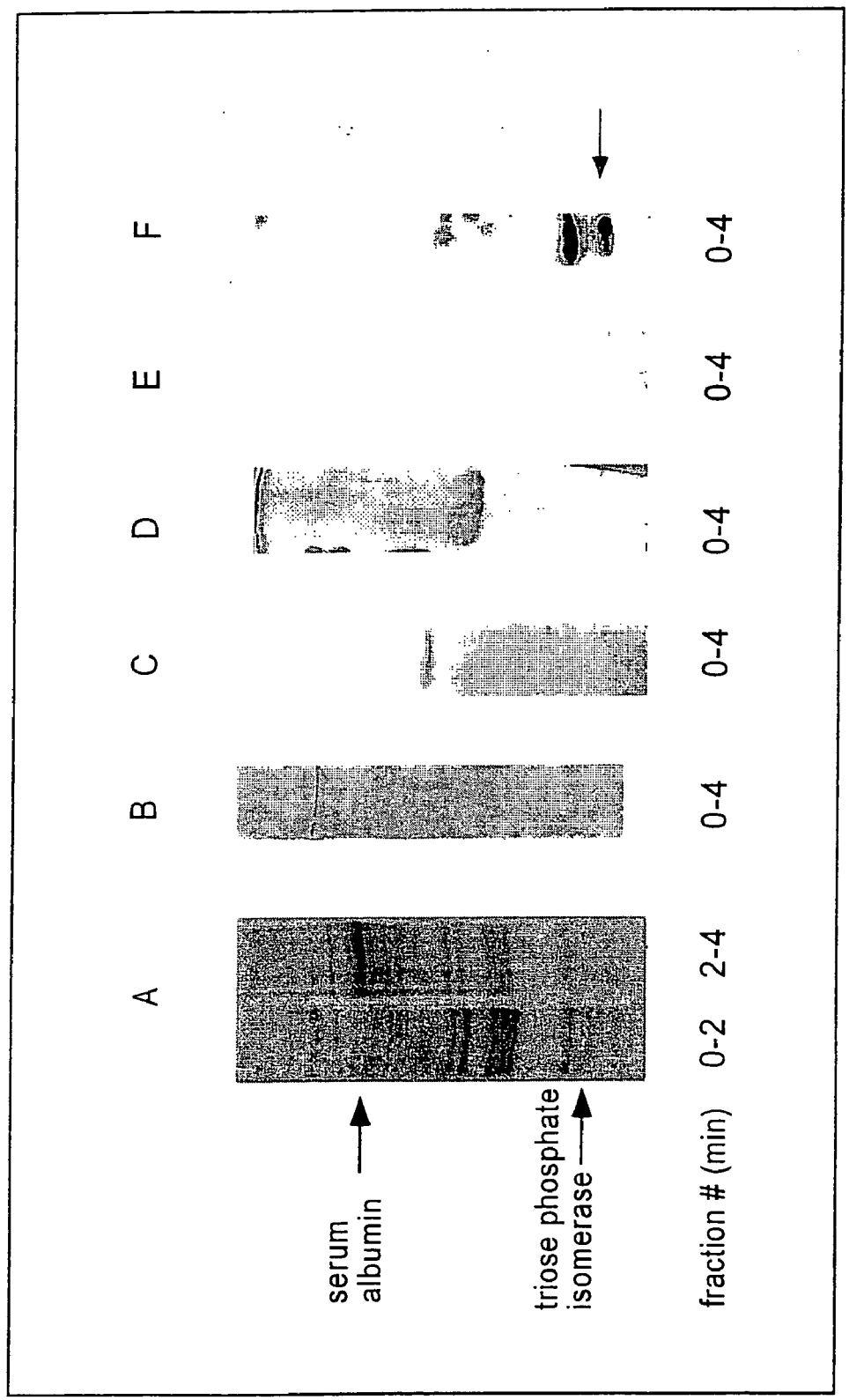
FIG. 1 shows the results of an SDS-PAGE analysis of reperfusion effluent from rat hearts which had undergone 15 min equilibration followed by 60 min of ischemia. Panel A shows 12.5% SDS polyacrylamide gel of the two minute effluent fractions collected at 0 and 2 min. Serum albumin and triose phosphate isomerase were identified by amino acid sequencing (Table 2). Panels B to F show western blots of the combined effluent fractions (0 to 4 min) probed with anti-a-actinin (panel B), anti-TnT (panel C), anti-tropomyosin (TM) (panel D), anti-TnI peptide P142T (residues 136 to 148) (MAb E2, panel E) and anti-MLC1 (panel F) antibodies. The MLC1 modification product is indicated by an arrow.

There is extensive controversy surrounding the use of cTnI as an indicator of MI. This controversy is mainly due to differences in the sensitivity and selectivity among various commercially available immunoassay diagnostic kits (Stromme et al. 1998, *Scand. J. Clin. Lab. Invest.* 58:693-699; Katrukha et al. 1998; *Clin. Chem.* 44:2433-2440). These differences arise from, at least in part, lack of mass standardization (Tate et al. 1999, *Clin. Chim. Acta.* 284:141-149; Shi et al. 1999, *Clin. Chem.* 45:1018-1025; Newman et al. 1999, *Clin. Chem.* 45:822-828), and heterogeneity in the cross-reactivity of the antibodies to various forms of cTnI (Wu et al. 1998, *Clin. Chem.* 44:1198-1208; Shi et al. 1999, *Clin. Chem.* 45:1018-1025). One major problem lies in the inability to determine the exact forms of cTnI present in a given serum sample, and the lack of a suitable purification or extraction procedure to isolate the cTnI.

To date, the consensus is that there is little free intact cTnI (Giuliani et al. 1999, *Clin. Chem.* 45:213-222; Wu et al. 1998, *Clin. Chem.* 44:1198-1208) present in blood, but rather the predominate form is a cTnI-cTnC complex (Giuliani et al. 1999, *Clin. Chem.* 45:213-222; Morjana et al. 1998, *Biotechnol. Appl. Biochem.* 28:105-111; Wu et al. 1998, *Clin. Chem.* 44:1198-1208), and some or all of the cTnI is proteolyzed from the C-terminus and/or the N-terminus. The modification progression of cTnI and its correlation with increasing severity of ischemia in rat the has been determined: cTnI is initially proteolyzed from the C-terminus (Van Eyk et al. 1998, *Circ. Res.* 82:261-271; McDonough et al. 1999, *Circ. Res.* 84:9-20), with loss of 17 amino acids with formation of protein-protein complexes between cTnI degradation products and cTnT or cTnC; this is followed by progressive N-terminal truncation (McDonough et al. 1999, *Circ. Res.* 84:9-20). Furthermore, it is these modification products, and not intact cTnI that are preferentially detected in the effluent from the severely ischemic, necrosis rat heart. In human myocardium, degradation and protein-protein complex formation is more extensive and complex, due in part to variation in stage and type of disease of patients.

The presence of cTnT in serum is also considered a biochemical marker of myocardial damage (Ravkilde 1998, *Dan. Med. Bull.* 45:34-50; Solymoss et al. 1997, *Clin. Cardiol.* 20:934-42) and comparisons with cTnI and CKMB suggest they are nearly equivalent (e.g., Mair et al. 1995, *Eur. J. Clin. Chem. Clin. Biochem.* 33:869-72; Stromme et al. 1998, *Scand. J. Clin. Lab. Invest.* 58:693-699) or that with CKMB and cTnI diagnosis of acute myocardial infarction is more rapid and has higher specificity (Penttila et al. 1997, *Eur. J. Clin. Chem. Clin. Biochem.* 35:767-74). In skeletal muscle injury, TnI, TnT and their various skeletal isoforms as well as tropomyosin and MLC are proteolyzed and undergo covalent complex formation. Skeletal TnI and other myofilament proteins and various modification products are detected in serum obtained from rats with respiratory fatigue/failure (due to breathing against a load). Thus there appears to be a similar or overlapping pathway for muscle damage in both cardiac and skeletal muscle.

The detection of myofilament protein modification products, in which those products are intact myofilament proteins, degradation products of myofilament proteins, and protein-protein complexes of myofilament proteins, in various biological samples such as blood, tissue, and urine, was described in detail in our co-pending U.S. patent application Ser. No. 09/115,589, filed Jul. 15, 1998. This prior application is incorporated herein by reference in its entirety. The present invention represents a substantial improvement in the analysis of myofilament proteins in biological samples in that it provides for the detection of chemical adducts of myofilament proteins (e.g., post-translational modifications) and various modifications thereof, including protein-protein complexes and protein fragments thereof. Heretofore, the detection of such chemical adducts of myofilament proteins in blood was not possible, and, although phosphorylated TnI was known to exist in muscle tissue, its significance with respect to muscle damage and heart disease was unknown. In accordance with the invention, progressive post-translational modification (e.g., phosphorylation) of myofilament proteins, their degradation and covalent complexes can be monitored, and correlated with extent of injury and type and stage of muscle damage (e.g., heart disease) of patients.

We have developed a method for detecting myofilament proteins such as troponins (TnI, TnT, TnC) and their modification products by western blot analysis of human serum directly (see Examples II and III, below). This method overcomes problems due to: 1) the large quantity of IgG and albumin which overwhelm the extremely small quantity of troponin; 2) manipulation of the serum used to either concentrate or isolate these proteins; and 3) bias and sensitivity limitations due to immunogenicity or detection methods. Using this method we have shown that, for example, TnI in the serum of patients following bypass surgery can be detected even below the level of TnI detected using currently available diagnostic kits. In one embodiment of this invention (see Example II, below), this method of western blot analysis was used to detect modified forms of TnI in serum from MI patients for up to 5 days following admittance to the emergency room, and to characterize changing patterns of TnI modification with the time course of MI.

According to a broad aspect, the invention provides a method for assessing muscle damage in a subject by obtaining a biological sample from the subject and evaluating the sample for the presence or absence of one or more myofilament protein modification products. Preferably, at least one of the myofilament protein modification products is a chemical adduct of a myofilament protein. More preferably, the chemical adduct is a phosphorylated form of troponin I, troponin T, or tropomyosin. The presence of one or more myofilament protein modification products, and in particular one or more chemical adduct(s) of a myofilament protein(s), is indicative of the extent and/or type of muscle damage in the subject. In one embodiment further described below, the relative amounts (i.e., levels) and types of myofilament protein modification products present in the biological sample are assessed as an indication of the extent of muscle damage in the subject.

In a preferred embodiment, the invention provides a method for assessing muscle damage in a subject by obtaining at least two biological samples from a subject at different times (i.e., not simultaneously), and evaluating the samples for a change with time in the presence or amount of one or more myofilament protein modification products. Preferably, at least one of the myofilament protein modification products is a chemical adduct of a myofilament protein. More preferably, the chemical adduct is a phosphorylated form of troponin I, troponin T, or tropomyosin.

The invention is based, in part, on the recognition that myofilament protein modification products are produced in a progressive and selective manner depending on the severity and nature of the ischemic/hypoxic insult, such that specific forms of myofilament protein modification products in a biological sample have diagnostic utility. That is, various myofilament protein modifications, such as phosphorylations, occur differentially with respect to a particular disease and its state. Thus, analysis of even a single biological sample in accordance with the invention can yield a wide range of information about the disease state of a subject. The invention further provides a method for monitoring the profile of one or more myofilament protein modification products with time, and relates such profile(s) to the progression/regression of the disease state of a subject. It is believed that the ability to characterize the profiles of one or more myofilament protein modification products, and in particular chemical adducts of myofilament proteins, in accordance with the present invention provides a new level of accuracy in diagnosing and assessing muscle damage.

According to this embodiment, a change with time in the presence or amount of one or more myofilament protein modification products is indicative of the extent or severity of the disease state of the subject. Also in accordance with this embodiment, such a change with time can be used to monitor the condition of a subject being treated for heart disease, and for evaluating the efficacy of treatments for such conditions. It will be appreciated that the number of biological samples obtained from a subject, and the time elapsed between samples, will vary in accordance with the condition of the subject and the diagnostic situation. For example, prior to and during heart surgery it is preferred to take multiple samples frequently, such as from 30 min to 2 h apart, to monitor the subject's response to the treatment. During recovery, biological samples can be taken less frequently, such as every 2 to 24 h. After recovery, samples can continue to be obtained even less frequently, such as once per month, to provide feedback as to the subject's condition, and thus to provide an indication of the efficacy of the surgery, or whether the subject is developing further complications, such as heart failure. In other situations, for example where a subject shows a predisposition for MI or HF, biological samples can be regularly obtained such as weekly, biweekly, or monthly, to determine the subject's prognosis on an on-going basis, and to evaluate the efficacy of any treatment(s) being administered to the subject. Furthermore, in the case of cardiac transplantation, patients can be monitored prior to surgery to determine the severity of their condition, and during surgery to detect the onset of rejection of the transplanted heart as well as the effectiveness of anti-rejection therapy. With heart transplantation a patient typically undergoes 10 to 20 biopsies in the first year. Monitoring changes in different post-translational myofilament protein modification products in the serum in accordance with the present invention could eliminate the need for biopsies. For respiratory (skeletal muscle) injury, identification of patients experiencing difficulty being weaned from respirators, or the degree of respiratory muscle damage with disease such as COPD or asthma, could be carried out in accordance with the invention either as single or multiple sequential assays. With sepsis, where there is multiple organ damage, or even heart failure, and where respiratory (skeletal) muscle injury can also occur, the invention provides for monitoring and differentiating both skeletal and cardiac muscle damage via assessing the level and quantity of post-translational modification of specific myofilament proteins, to assess severity of disease.

In so far as the formation of chemical adducts such as phosphorylated myofilament proteins serves a protective role during ischemic or hypoxic events, for instance by minimizing or preventing degradation of the myofilament proteins involved, the invention contemplates a method for minimizing muscle damage during such events by enhancing the formation of chemical adducts. For example, in the case of phosphorylated TnI, where known kinases are involved, a method for enhancing the formation of chemical adducts in accordance with the invention involves upregulation of one or more of those kinases to increase phosphorylation, such as by administering to a subject a therapeutically effective amount of a kinase activating or stimulating agent(s), which enhances the ability of a kinase to phosphorylate its substrate. Similarly, an agent(s) that inhibits one or more phosphatases can also be employed. The method can be applied, for example, prior to invasive procedures such as heart surgery, to mitigate any myocardial damage resulting therefrom.

In addition, the invention further contemplates modulating muscle cell function (e.g., increasing or decreasing contractile strength or efficiency) using such methods. Thus, in other therapeutic situations it may be desirable to suppress the formation of chemical adducts of myofilament proteins. Using the example of phosphorylated TnI, administration to a subject of a therapeutically effective amount of an agent(s) which inhibits the kinase(s) involved, and/or an agent(s) which activates an appropriate phosphatase(s), are suitable procedures in accordance with this embodiment of the invention. In the case of TnI, a suitable kinase inhibitor is, for example, an agent which binds to or blocks any of the phosphate binding sites (kinase domains) on TnI (see below). Kinase and phosphatase modulating agents can be, for example, drugs, antibiotics, enzymes, chemical compounds, biological macromolecules, and analogues thereof, and can be administered using known techniques such as injection. Modulation of kinase and/or phosphatase activity can also be achieved through gene therapy techniques. The modulation achieved using any such technique can be partial or complete.

As used herein, the following terms and phrases are intended to have the definitions provided below:

The phrase "myofilament protein" is defined as any protein associated with the contractility of a skeletal or cardiac muscle cell. Myofilament proteins include, but are not limited to, α-actinin, desmin, actin, myosin binding protein C, tropomyosin, troponins (e.g., troponin I, troponin T, troponin C), and myosin light chain 1, 2, and 3. The abbreviations TnI, TnT, and TnC refer to those troponins generally, while cTnI, cTnT, and cTnC refer to cardiac troponins and sTnI, sTnT, and sTnC refer to skeletal troponins.

The phrase "chemical adducts" or "chemical adducts of myofilament protein(s)" is defined as a peptide species formed by bonding, for example covalent bonding, of a polypeptide or a polypeptide fragment and a different compound. For purposes of this disclosure, chemical adducts do not include covalent linkage of two similar species, i.e., protein-protein, complexes. However, a chemical adduct which is the linkage of a different chemical compound or moiety to a protein-protein complex or a protein degradation product is encompassed by this definition of chemical adduct. Chemical adducts known in the art relating to post-translational modification of proteins include, but are not limited to, phosphorylation, glycosylation, myristylation, phenylation, acetylation, nitrosylation, s-glutathiolation, amidation, biotinylation, c-mannosylation, flavinylation, farnesylation, formylation, geranyl-geranylation, hydroxylation, lipoylation, methylation, palmitoylation, sulphation, gamma-carboxyglutamic acids, N-acyl diglyceride (tripalmitate), O-GlcNAc, pyridoxal phosphate, phospho-pantetheine, and pyrrolidone carboxylic acid. Preferred chemical adducts are phosphorylation, glycosylation, myristylation, phenylation, acetylation, nitrosylation, and sulphation. Chemical adducts of myofilament proteins include such post-translational modification of intact myofilament proteins, of degradation products of myofilament proteins, and of protein-protein complexes of myofilament proteins.

The phrase "degradation product" is defined as any fragment of a myofilament protein. Degradation products can be produced by, for example, proteolysis. Examples of degradation products of myofilament proteins are peptide fragments including all or a portion of the carboxyl-terminal region consisting of amino acids 194 to 210 (rat sequence) of cardiac troponin I, or all or a portion of the amino-terminal region consisting of amino acids 1 to 193 of troponin I (rat cardiac TnI amino acid sequence) (referring to the sequence published in any one of Vallins et al. 1990, *FEBS Lett.* 270: 57-61; Armour et al. 1993, *Gene,* 131:287-292, or Hunkeler et al. 1991, *Circ. Res.,* 69:1409-14). Further examples are peptide fragments of myosin light chain 1, such as all or a portion of the carboxyl-terminal region consisting of amino acids 20 to 199 of cardiac myosin light chain 1, or all or a portion of the amino-terminal region consisting of amino acids 1 to 19 of myosin light chain 1 (referring to the sequence published in Zimmermann et al. 1990, *J. Mol. Biol.* 211(3):505-513). As defined herein, "degradation products" also includes myofilament proteins modified by processes such as, for example, oxidation and deamidation.

The phrase "protein-protein complex" is defined as any complex of two or more intact myofilament proteins or fragments thereof, or any complex of a myofilament protein or fragment thereof with another protein or fragment thereof. Examples of such complexes involving protein fragments include those formed from, for example: TnI (amino acids 1 to 193) with TnT (amino acids 191 to 298); and TnI (amino acids 1 to 193) with TnC (amino acids 1 to 94).

The phrase "myofilament protein modification product" is a general term defined as any modification of a myofilament protein associated with muscle damage. Myofilament protein modification products can be chemical adducts of myofilament proteins, degradation products of myofilament proteins, and protein-protein complexes of myofilament proteins.

The term "muscle damage" is defined as cellular damage in skeletal muscle and in the myocardium as a result of hypoxia, hypoxemia, ischemia and/or ischemia/reperfusion injuries, as well as any insult or stress that activates or is associated with activation of a protease and/or a cross-linking enzyme such that modification (e.g., cross-linking, degradation) of cardiac myofilament proteins occurs. Muscle damage may be acute, where it can result from any brief (acute) ischemic/hypoxic period (e.g., 30 seconds to 2 days) such as stunning, or pre-conditioning such as infarction (e.g., myocardial infarction (MI)), unstable angina and the like. In some cases, such as in stunning, acute muscle damage may be reversible. Muscle damage may also be chronic, where it can result from longer (chronic) ischemic/hypoxic episodes (e.g., durations of days to years), such as heart failure (HF) and diabetes. Chronic muscle injury includes situations where muscle injury (e.g., due to necrosis or apoptosis and loss of muscle cells) causes the muscle to have to compensate for loss of functioning muscle cells. This leads to hypertrophy or atrophy of the muscle. Under these conditions, post-translational modification occurs to specific myofilament proteins in a time dependent manner.

The methods of the present invention are applicable to acute and chronic muscle damage. Moreover, as described in detail below, the methods of the invention can be used to diagnose not only whether a subject has experienced muscle damage, but also whether that damage is acute or chronic. This is achieved in the invention by providing for the detection and characterization of a suite of myofilament protein degradation products, and associating specific or unique degradation products with either acute or chronic muscle damage. For example, a biological sample containing protein-protein complexes involving TnI of which only a small proportion (e.g., less than 10%) are phosphorylated would indicate acute muscle damage, such as that resulting from MI or unstable angina. If, however, analysis of a biological sample revealed a much greater proportion (e.g., about 50%) of such phosphorylated TnI complexes or the phosphorylation of a specific amino acid residue, this would indicate chronic muscle damage such as that resulting from HF. Of course, any analysis of a biological sample in accordance with the invention preferably involves detecting a plurality of myofilament protein degradation products, to provide a more comprehensive diagnosis. Thus, in the above examples, the diagnosis of acute muscle damage could additionally be based on the detection of, for example, small degradation products in abundance in the sample, while the diagnosis of chronic muscle damage could additionally be based on the detection of modification products involving other myofilament proteins such as TnT.

Chronic injury to the heart will cause remodelling and hypertrophy, with loss via necrosis or apoptosis therefore allowing monitoring by serum samples and when possible tissue samples (at time of heart surgery if appropriate). Low levels of myofilament proteins and their modification products and chemical adducts can be detected in blood and presence or quantity or quality of a myofilament protein(s) or its modification product indicate stage of disease. TnI and other myofilament proteins are modified both at gene level (upregulation) and with post-translational modification including phosphorylation and possibly glycosylation at unique sites compared to those with acute injury (right after injury). For example, an increase in amount of TnC in tissue (and therefore the amount present in blood) correlates with a decrease in heart function. In other words, the more TnC present the lower the cardiac output or ejection fraction. TnT does not undergo an isoform switch (in swine ischemic induced HF) but there is a large increase in its pI (from ~4.5 to 6.5) due to a post-translational modification.

Ischemia/reperfusion injury ranges from mild to severe. The terms "mild ischemia" and "mild ischemia/reperfusion injury" refer to situations in which reversible damage to the myocardium has occurred. In these situations, the heart can eventually regain the ability to contract and a full recovery is possible. Usually, in such situations, the majority of the cells comprising the affected muscle retain integrity of the cellular membrane. Mild myocardial ischemia and/or ischemia/reperfusion injury are marked by the presence of one or more of a cardiac troponin I modification product(s) (e.g., amino acid residues 1 to 193), the loss of $\alpha$-actinin, and the formation of a protein complex(es). Specific and selective phosphorylation of cTnI, and other myofilament proteins, occurs rapidly with ischemia. For instance, within 5 minutes of ischemia in the in vivo canine model, TnI is phosphorylated at up to 2 amino acid residues. This increases following reperfusion, and the phosphorylation status changes even after 3 hours post-reperfusion. Therefore, phosphorylation of cTnI is dynamic and represents the status of injury. Some of these phosphorylation sites are unique to specific proteolyzed or protein-protein complexes.

The terms "severe ischemia" and "severe ischemia/reperfusion injury" refer to situations where irreversible damage to the myocardium has occurred, i.e., situations where the muscle cannot regain its full ability to contract. Usually, in such situations, there is a loss of cellular membrane integrity and cellular proteins are released and necrosis occurs. Severe myocardial ischemia and/or ischemia/reperfusion injury are often marked by the presence of one or more of a myosin light chain 1 modification product(s) (e.g., amino acid residues 20 to 199), an additional TnI modification product(s) (e.g., amino acid residues 63 to 193, amino acid residues 73 to 193), TnT modification product(s), (e.g., both protein-protein complexes and degradation products, and their phosphorylation state or other chemical aducts) and $\alpha$-actinin modification product(s).

The term "ischemia" refers to anemia (lack of oxygen delivery) in a tissue due to obstruction of the inflow of arterial blood. The term "hypoxemia" refers to a state in which the oxygen pressure and/or concentration in arterial and/or venous blood is lower than its normal value at sea level (Bartels et al. 1973, *J. Appl. Physiol.* 34:549-558) and includes "hypoxia" (reduced level of oxygen in inspired gas). Hypoxemia may or may not be associated with insufficient blood flow.

The term "ischemia/reperfusion injury" refers to injury due to both ischemia, as defined above, and subsequent attempts to provide oxygen by forcing oxygenated blood through the blood vessels.

The term "biological sample" is intended to include any sample obtained from a subject which may contain a myofilament protein modification product as defined above detectable by the methods of the present invention. In one embodiment, the biological sample is a sample of a tissue derived from a subject, preferably a sample of a cardiac or skeletal muscle tissue. The sample can be a whole tissue or part of a tissue retaining the myofilament protein modification product. For example, a small biopsy tissue from a subject undergoing heart surgery or a sample obtained via catheterization following heart transplantation can be used in the method of the invention. Alternatively, the biological sample can be a biological fluid such as whole blood, serum, plasma, lymphatic fluid, amniotic fluid, cerebrospinal fluid, urine, and the like. Fluid extracts of tissues such as heart or skeletal muscle can also be used in the method of the present invention. The preferred biological fluid for this invention, however, is bloods serum or urine.

The term "subject" is intended to include any mammal susceptible to myocardial damage (e.g., horses, dogs, humans). In a preferred embodiment, the subject is a primate. In an even more preferred embodiment, the primate is a human.

The term "obtaining" is intended to include recovery of a biological sample from a subject in a way such that the myofilament protein modification product(s) is retained in a form that can be recognized by a compound specific for the myofilament protein modification product(s). Biological samples can be obtained from a subject using methods known in the art. For example, blood can be drawn from a subject suffering from heart failure or a biopsy tissue can be obtained from a subject undergoing heart surgery or catheterization, using standard techniques.

Assessment of muscle damage in a biological sample can be performed by incubating the biological sample with a compound specific for one or more myofilament protein modification product(s), under conditions which allow the compound to form a complex with the myofilament protein modification product, and then detecting the complex, for example, by assaying for the presence of a label attached to the compound.

Assessment of myocardial or skeletal muscle damage in a biological sample can be performed by direct detection of myofilament protein modification product(s) in the sample, using, for example, chromatography techniques such as HPLC, electrophoresis, ELISA, RIA analysis (immunological detection), or peptides or proteins that bind to myofilament proteins. These analyses are used to detect differences between elution profiles of samples obtained before and after, for example, treatment of hypoxemia, hypoxia, ischemia or ischemia/reperfusion. As well, the appearance or disappearance of one or more myofilament protein modification products, such as chemical adducts, peptides, or fragments, such as, for example, phosphorylated versus non phosphorylated intact human cardiac TnI or TnI residues 1-192 or 193-209 (or any C-terminal and/or N-terminal fragment), or myosin light chain 1 residues 1 to 19, in the elution profiles obtained during HPLC analysis can be used as indicators of muscle damage.

It will be appreciated that, for purposes of detecting specific myofilament protein modification products in accordance with the invention, using standard techniques, phospho-specific antibodies can be produced that recognize phosphorylated or non-phosphorylated versions of, for example, TnI, TnT, and tropomyosin and their degradation products. Further, specific antibodies can be produced that only recognize specific phosphorylated amino acid residues. The latter is important for determining whether a particular residue or novel site is involved, and for assessing the type and state of a disease.

Prescreening of biological samples such as urine or tissue homogenates can be used to detect high (e.g., above 32 kDa) or low (e.g., below 20 kDa) molecular weight myofilament protein modification products, peptides, or fragments, in the samples, can also be performed using, for example, specific molecular weight cut-off membranes (e.g., dialysis tubing, filters). The presence one or more myofilament protein modification products, in particular TnI or TnI fragments, protein-protein complexes, and chemical adducts and/or an increase in the quantity of total protein (due to the presence of such complexes or proteolytic fragments) in either the high or low molecular weight fraction would indicate muscle damage or whether these products are phosphorylated, or phosphorylated at a specific amino acid residue.

As used herein the term "compound" is intended to include any agent which specifically recognizes and binds to an intact myofilament protein and/or a modification product thereof as defined herein. For example, the compound can be an antibody, a target protein, a peptide or a peptidomimetic, either synthetic or native, labelled or unlabelled. The term "specifically binds" means binding to a particular intact myofilament protein (e.g., troponin I) and/or a modification product thereof (e.g., human cardiac TnI residues 1 to 192, protein-protein complex comprising myofilament fragments such as TnI residues 1 to 192 with TnT residues 191 to 298, or protein-protein complex comprising, for example, intact TnI and TnT, such as a 66 kDa complex found in skeletal muscle or human cardiac biopsy) without substantially binding to any other intact myofilament protein and/or a modification product thereof present in the biological sample. The term "antibody" as used herein encompasses all forms of antibodies known in the art, such as polyclonal, monoclonal, chimeric, recombinatorial, single chain and humanized antibodies, as well as functional fragments thereof (e.g., F(ab')$_2$ fragments), either synthetic or native, labelled or unlabelled, which specifically bind to a myofilament protein modification product. Binding between the compound and the myofilament protein modification product can be covalent or, preferably, non-covalent. When the myofilament protein modification product is a covalent complex, the compound can be a recombinant, native, or synthetic peptide or fragment thereof that recognizes a region or a portion of a region of the complex corresponding to the covalent bond.

In one embodiment, the compound is a monoclonal antibody which recognizes one or more myofilament protein modification product(s). The antibodies can be recombinant, synthetic, or native, fragments or intact, screened to recognize the myofilament protein modification product(s) of interest. Monoclonal antibodies capable of recognizing myofilament protein modification products of the invention can be prepared using methods well known in the art. Such methods are described, for example, in detail in U.S. Pat. No. 4,942,131 to Yamasaki et al., issued Jul. 17, 1990, and U.S. Pat. No. 5,583,053 to Kim, issued Dec. 10, 1996. The term "monoclonal antibody," as used herein, refers to a population of antibody molecules that contain only one species of an antigen binding site capable of immunoreacting with a particular epitope of a myofilament protein modification product. Said epitope may also be present in intact myofilament protein. A monoclonal antibody composition thus typically displays a single binding affinity for a myofilament protein modification product.

Monoclonal antibodies useful in the methods of the invention are directed to an epitope of a myofilament protein modification such that the complex formed between the antibody and the myofilament protein modification product can be recognized in detection assays such as ELISA, RIA etc. A monoclonal antibody to an epitope of a myofilament protein modification product can be prepared by using a technique which provides for the production of antibody molecules by continuous cell lines in culture. These include but are not limited to the hybridoma technique originally described by Kohler and Milstein (1975, *Nature* 256:495-497), and the more recent human B cell hybridoma technique (Kozbor et al. 1983, *Immunol Today* 4:72), EBV-hybridoma technique (Cole et al. 1985, *Monoclonal Antibodies and Cancer Therapy*, Alan R. Liss, Inc., pp. 77-96), and trioma techniques. Other methods which can effectively yield monoclonal antibodies useful in the present invention include phage display techniques (Marks et al. 1992, *J. Biol. Chem.:* 16007-16010).

In one embodiment, the antibody preparation applied in the subject method is a monoclonal antibody produced by a hybridoma cell line. Hybridoma fusion techniques were first introduced by Kohler and Milstein (Kohler et al. 1975, *Nature*

256:495-97; Brown et al. 1981, *J. Immunol.* 127:539-46; Brown et al. 1980, *J. Biol. Chem.* 255:4980-83; Yeh et al. 1976, *PNAS* 76:2927-31; and Yeh et al. 1982, *Int. J. Cancer* 29:269-75). Thus, the monoclonal antibody compositions of the present invention can be produced by immunizing an animal with a myofilament protein modification product. The immunization is typically accomplished by administering the myofilament protein modification product to an immunologically competent mammal in an immunologically effective amount, i.e., an amount sufficient to produce an immune response. Preferably, the mammal is a rabbit or a rodent such as a rat or a mouse. The mammal is then maintained for a period sufficient for the mammal to produce cells secreting antibody molecules that immunoreact with the myofilament protein modification product. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay. These screening methods are well known to those of skill in the art, e.g., ELISA, flow cytometry, and/or the Dipstick by Spectral Diagnostics Inc, Toronto, Canada.

A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred and can be mechanically separated into individual cells in a physiologically tolerable medium using methods well known in the art. Mouse lymphocytes give a higher percentage of stable fusions with the mouse myelomas described below. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Manassas, Va.

The resulting cells, which include the desired hybridomas, are then grown in a selective medium, such as HAT medium, in which non fused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the myofilament protein modification product antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. 1982, in: *Monoclonal Hybridoma Antibodies: Techniques And Applications*, Hurell (ed.), CRC Press, pp. 51-52). Hybridomas produced according to these methods can be propagated in vitro or in vivo (in ascites fluid) using techniques known in the art.

Monoclonal antibodies or fragments thereof suitable for use in the present invention (i.e., which recognize and specifically bind to myofilament protein modification products) can also be produced by other methods well known to those skilled in the art of recombinant DNA technology. Such alternative methods include the "combinatorial antibody display" method in which antibodies and antibody fragments having a particular antigen specificity are identified and isolated, and can be utilized to produce monoclonal anti-myofilament protein modification product antibodies (for descriptions of combinatorial antibody display see e.g., Sastry et al. 1989, *PNAS* 86:5728; Huse et al. 1989, *Science* 246:1275; and Orlandi et al. 1989, *PNAS* 86:3833). After immunizing an animal with a myofilament protein modification product immunogen as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers corresponding to a conserved 3' constant region primer can be used for PCR amplification of the heavy and light chain variable regions from a number of murine antibodies (Larrick et al. 1991, *Biotechniques* 11:152-156). A similar strategy can also been used to amplify human heavy and light chain variable regions from human antibodies (Larrick et al. 1991, *Methods: Companion to Methods in Enzymology* 2:106-110).

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a variegated anti-myofilament protein modification product antibody display library can be found in, for example, Ladner et al., U.S. Pat. No. 5,223,409; Kang et al., International Publication No. WO 92/18619; Dower et al., International Publication No. WO 91/17271; Winter et al., International Publication WO 92/20791; Markland et al., International Publication No. WO 92/15679; Breitling et al., International Publication WO 93/01288; McCafferty et al., International Publication No. WO 92/01047; Garrard et al., International Publication No. WO 92/09690; Ladner et al., International Publication No. WO 90/02809; Fuchs et al. 1991, *Bio/Technology* 9.1370-1372; Hay et al. 1992, *Hum Antibod Hybridornas* 3:81-85; Huse et al. 1989, *Science* 246:1275-1281; Griffiths et al. 1993, *EMBO J.* 12:725-734; Hawkins et al. 1992, *J Mol Biol* 226:889-896; Clackson et al. 1991, *Nature* 352:624-628; Gram et al. 1992, *PNAS* 89:3576-3580; Garrad et al. 1991, *Bio/Technology* 9:1373-1377; Hoogenboom et al. 1991, *Nuc Acid Res* 19:4133-4137; and Barbas et al. 1991, *PNAS* 88:7978-7982.

In an alternative embodiment, the compound is a peptide or a peptidomimetic. As used herein, the term "peptide" encompasses any protein or protein fragment which specifically recognizes and binds a myofilament protein modification product. For example, the peptide can be derived from a troponin C protein. As used herein, the term "peptidomimetic" is intended to include peptide analogs which serve as appropriate substitutes for peptides in interactions with, e.g., receptors and enzymes. The peptidomimetic must possess not only affinity, but also efficacy and substrate function. That is, a peptidomimetic exhibits function(s) of a peptide, without restriction of structure. Peptidomimetics of the present invention, i.e., analogs of peptides which specifically bind to myofilament protein modification products, include amino acid residues or other moieties which provide the functional characteristics described herein. Peptidomimetics and methods for their preparation and use are described in Morgan et al. 1989, "Approaches to the discovery of non-peptide ligands for peptide receptors and peptidases," In *Annual Reports in Medicinal Chemistry* (Virick, F. J., ed.), Academic Press, San Diego, Calif., pp. 243-253.

Prior to incubation with the biological sample and complexing with a myofilament protein modification product in the sample, the compound can be immobilized on a suitable solid phase surface by various methods known to those skilled in the art. The solid surface can be selected from a variety of materials including plastic tubes, beads, microtiter plates, latex particles, magnetic particles, cellulose beads, agarose beads, paper, dipsticks, and the like. The methods for immobilizing the compound are not narrowly critical, and could include passive absorption, covalent linkage, physical trapping, and the like. In general, the compound can be absorbed onto the solid support as a result of hydrophobic interactions between non-polar protein substructures and non-polar support matrix material.

As used herein the language "label" is intended to include any observable or measurable moiety which can be directly or indirectly attached to a complex formed between the compound and the myofilament protein modification product so that the complex can be detected.

For example, the label can be a direct label which, in its natural state, is readily visible, either to the naked eye, or with the aid of an optical filter and/or applied stimulation, e.g. U.V. light to promote fluorescence. Examples of coloured labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A) 280 559 and 0 281 327); or dyes encapsulated in liposomes as described in Campbell et al. (U.S. Pat. No. 4,703,017). Other direct labels include a radionucleotide, a fluorescent moiety or a luminescent moiety. In addition to these direct labelling devices, indirect labels including enzymes can also be used according to the present invention. Various types of enzyme linked immunoassays are well known in the art, for example, alkaline phosphatase, horseradish peroxidase, luciferase, beta-galactosidase, lysozyme, glucose-6-phosphate dehydrogenase, lactate dehydrogenase, and urease. These immunoassays and others have been discussed in Engvall et al. 1980, Enzyme Immunoassay ELISA and EMIT, *Methods in Enzymology*, 70:419-439 and in U.S. Pat. No. 4,857,453.

Reagents for assessing the extent of myocardial damage in a biological sample obtained from a subject can be assembled in a kit suitable for commercial manufacture and sale. The kit can include, e.g., in separate containers, compounds specific for myofilament protein modification products and reagents appropriate for the formation and detection of the complex formed between the compound and the myofilament protein modification product. The compound can be an antibody, peptide or peptidomimetic. The compound in the kit can also be immobilized on a solid phase and can be labelled. If an enzyme label is used, the kit can further include the enzyme substrate. The kit can still further include appropriate standards, positive and negative controls and instructions for performing the assay. In other embodiments the kit can include any items and/or reagents required for direct detection of myofilament protein modification product(s) using, for example, HPLC or molecular sieve techniques.

In yet another embodiment, the invention provides a method for screening for an agent which modulates the level of a myofilament protein modification product present in a biological sample. The method involves providing a biological sample containing a myofilament protein modification product, from a subject, contacting at least a portion of the biological sample with a test agent and determining the effect of the test agent on the level of the myofilament protein modification product in the so-contacted biological sample.

As used herein the term "test agent" is intended to include an agent that modulates the levels of a myofilament protein modification product in a biological sample, such as a calcium sensitizer. Such agents can be, for example, a drug, an antibiotic, an enzyme, a chemical compound, a mixture of chemical compounds, a cardioplegic solution, a biological macromolecule, and analogs thereof.

The level of the myofilament protein modification product can be determined using a compound which binds specifically to the myofilament protein modification product, using the methods described above.

In many drug screening programs which test libraries of modulating agents and natural extracts, high throughput assays are desirable in order to maximize the number of modulating agents surveyed in a given period. Assays which are performed in cell-free systems, such as may be derived with cardiac muscle cell extracts, or from purified or recombinant proteins and/or peptides, are preferred as "primary" screens in that they can be generated to permit rapid development and relatively easy detection of an alteration in the level of a myofilament protein modification product, which is mediated by a test modulating agent. Moreover, the effects of cellular toxicity and/or bioavailability of the test modulating agent can be generally ignored in the in vitro system, the assay instead being focussed primarily on the effect of the test agent on the levels of a myofilament protein modification product(s).

The invention thus provides for the use of myofilament protein modification products in drug screening tests and tests for assessing the efficacy of treatments and interventions on patients that experience muscle dysfunction due to hypoxia, hypoxemia, ischemia, and/or reperfusion damage. Further, transgenic animals or cell lines expressing or transfected with one or more myofilament protein modification products could be used to mimic hypoxic, hypoxemic, ischemic and/or reperfusion damage, and provide valuable tools for carrying out such screening tests and evaluation of treatments. In addition, in vitro assays with purified proteins, peptides, or fragments, isolated myofilaments, cells, or skinned muscle fibers in which one or more myofilament protein modification product(s) is present can similarly be used.

The efficacy of test agents can be assessed by generating dose response curves from data obtained using various concentrations of the test modulating agent. Moreover, a control assay can also be performed to provide a baseline for comparison. In the control assay, the biological sample containing a myofilament protein modification product is incubated in the absence of a test agent.

In a preferred embodiment, the agent being screened for is a calcium sensitizer, (i.e., an agent that increases the sensitivity of striated muscle cells to calcium), or desensitizer, depending on the particular situation.

In yet another aspect, the invention provides a method for assessing the extent (e.g., mild to severe, as defined herein) or type (e.g., reversible or irreversible, as defined herein) of skeletal muscle or myocardial damage in a biological sample obtained from a subject. The method involves obtaining a biological sample from the subject, and incubating the biological sample with at least one compound (e.g., antibody) which specifically binds to one or more different myofilament proteins or myofilament protein modification products present in the sample, under conditions which allow the compound to form one or more complexes with the myofilament proteins or myofilament protein modification products. The method further involves detecting formation of the complexes and then characterizing the profile of the one or more myofilament proteins or myofilament protein modification products contained in the complexes as an indication of the extent or type of skeletal muscle or myocardial damage in the subject.

In certain embodiments, the formation of complexes is detected using ELISA, RIA, immunoblot ("western blot") analysis, HPLC analysis, PAGE analysis (SDS or native), or 2-D electrophoresis or IEF 1-D electrophoresis. These methods are known in the art and are described below in the "Examples" section.

Characterizing the profile of different myofilament proteins or myofilament protein modification products (which can be from the same or from different myofilament proteins) can be achieved either qualitatively or quantatively. Qualitative characterization involves comparing the sizes of the proteins and modification products and quantative characterization involves quantifying and comparing their relative amounts. Furthermore, tracing the phosphorylation or other post-translational modification to a specific amino acid residue or residues can be achieved for differentiating stages or types of disease.

For example, when qualitatively characterizing different myofilament proteins and/or modification products present in the biological sample, antibodies can be used which differentially recognize epitopes present in the various modification products. Using a label that has a measurable moiety attached to it (e.g., b-galactosidase), a profile or "fingerprint" of the proteins and modification products can be obtained. This profile, which is expected to include, for example, characteristic ratios of various proteins and/or fragments from the same (e.g., cardiac TnI residues 1 to 193 vs. cardiac TnI residues 63 to 193) or from different (e.g., TnI vs. myosin light chain 1) proteins, can then be associated with a level (i.e., extent) or type of myocardial damage. In addition, the quantity of phosphorylated vs dephosphorylated forms of TnI or other myofilament proteins can indicate severity of disease, time from initial insult, or the extent of damage that has occurred. For example, the appearance of covalent complexes or small TnI fragments may indicate chronic long term damage to the heart. Identifying phosphorylation of many residues or specific amino acid residues also helps in stratifying the severity or type of disease. Chemical modifications other than phosphorylation occur to myofilament proteins, in particular to TnT with certain disease states.

Different myofilament proteins and/or modification products present in the biological sample can also be quantitatively characterized (e.g., compared to a standard). For example, levels of different troponin I modification products (e.g., a cardiac troponin T fragment consisting of amino acids 1 to 193) can be compared to one another, or to levels of the intact troponin I protein, and this pattern of protein levels can be associated with a level (i.e., extent) or type of myocardial damage. Levels of myofilament proteins and/or modification products, or the modification of a specific amino acid residue(s) can be detected using for example quantifiable labels (e.g., antibodies labelled with an enzyme, the activity of which can be measured and correlated with levels of antibody binding), as are known in the art, which specifically bind to the proteins and/or modification products.

In one embodiment, the method of the invention is used to diagnose mild ischemia by detecting the presence of phosphorylated skeletal or cardiac troponin I or TnI fragments (e.g., cardiac TnI residues 1 to 193) and comparing the levels of this fragment to the levels of intact troponin I and/or comparing levels of phosphorylated to dephosphorylated forms. The quantity of each modification product and chemical adduct, or of the exact amino acid residues that have been modified can also be determined. For example, in isolated rat hearts with mild ischemia (stunning), a TnI 22 kDa degradation product is phosphorylated at a site that is not phosphorylated in the intact protein. As well, phosphorylated TnI and/or its proteolytic fragments may appear in blood or form prior to the unphosphorylated TnI or its proteolytic fragments or protein-protein complex.

More severe ischemic injury would involve detection of TnI proteolyzed at the N-terminus or specifically phosphorylated at the N-terminus. With chronic conditions, TnI protein-protein complex is heavily phosphorylated and present in larger quantities than immediately following injury. Furthermore, TnT and other myofilament proteins undergo both upregulation (increase in quantity) and specific phosphorylation that may not occur during acute injury.

As the invention shows linkage or correlation between the modifications of specific myofilament proteins and the degree of myofilament/muscle damage that has occurred, the profile at a given time point of the specific modifications to several myofilament proteins provides an indication of the extent of muscle damage that has occurred. Both the type of modification of a particular protein(s) and the quantity of a particular protein modification product(s) change over time, and can be used to characterize the level of damage that has occurred.

Different myofilament proteins are more or less susceptible to modification depending on the extent of ischemic or ischemia/reperfusion injury that has occurred. Thus, the appearance of a certain modification to a specific protein can be used as a marker/index for extent of muscle damage. For example, TnT, TnI, $\alpha$-actinin, or MLC1 degradation (residues 20 to 199) occurs only with very severe ischemia in the myocardium. Therefore, if one detects smaller fragments of TnT, TnI, $\alpha$-actinin or MLC1 in a biological sample, it is an indication that the myocardium is severely and possibly irreversibly damaged.

Moreover, it is useful to study in parallel the profiles presented by different myofilament proteins and their products. By monitoring several proteins simultaneously, and determining the quantity and quality of the various species of these proteins, a finer analysis, and potentially more accurate assessment, can be made. The quantity as well as the appearance of the various modifications in a particular sample type is expected to be diagnostic for each increment along the pathway from mild to severe muscle damage. For example, in a tissue sample from myocardium, the following changes would be expected over time as severity of injury increased:
1. TnI phosphorylation.
2. TnI degradation product from the C-terminus of TnI (probably producing residues 1 to 192) and loss of $\alpha$-actinin. Possibly preferential phosphorylation of the degradation product at one or more amino acid residues.
3. TnI or TnI 1 to 193 protein-protein complex formation. (As protcolysis and protein-protein complex formation may occur very rapidly the two species may thus be indistinguishable from one another.) Importantly, there appears to be a unique and possibly novel phosphorylation that occurs with these species (residue 122, 128 or 142) that does not occur with the intact protein.

4. Other phosphorylation of all TnI. The covalent complex is most heavily phosphorylated; over 7 sites, although this extensive phosphorylation status might occur over time indicating long term or chronic injury to the heart.
5. TnI is further degraded from the N-terminus (possibly residues 63 to 193), with the products being phosphorylated.
6. Further degradation of TnI from the N-terminus (possibly residues 73 to 193). NOTE: with the products being phosphorylated.
7. TnT degradation.
8. MLC1 degradation (residues 20 to 199).
9. Appearance of these protein species in blood, as opposed to only in the myocardium tissue sample. It is expected that these proteins and protein modification products would also be observed in urine at this level of severity of damage. It is also expected that in blood the phosphorylated forms appear first. Most patients have only intact TnI and 1 degradation product (expected to be similar to 1-193) in phosphorylated and some dephosphorylated forms. In the minority of patients smaller degradation products (which are phosphorylated) and/or covalent complexes (which are also phosphorylated) are also present.

The invention is further illustrated by the following examples, which should not be construed as further limiting. The contents of all references, pending patent applications, and published patents cited throughout this application are hereby expressly incorporated by reference.

EXAMPLE I

Rat Cardiac Muscle

Perfusion of Isolated Rat Hearts

Cardiac function was measured in a non-recirculating Langendorff perfusion apparatus. Rats (250 to 350 g) were anaesthetized with sodium pentobarbital (50 mg/kg) and injected with heparin (200 units) before the heart was excised. The hearts were quickly excised and placed in ice cold saline. The aorta was cannulated with a 1.6 mm glass cannula (Radnoti Glass Inc.) and perfused in a non-recirculating apparatus with heart chamber (Radnoti Glass Inc.) at a coronary flow of 14 ml/min with Krebs Ringer bicarbonate buffer equilibrated with 95% $O_2$ and 5% $CO_2$ at 37° C. The Krebs Ringer bicarbonate buffer consisted of 100 mM sodium chloride, 4.74 mM potassium chloride, 1.18 mM potassium dihydrogen phosphate, 1.18 mM magnesium sulfate, 1.15 mM calcium chloride, 25 mM sodium bicarbonate, 11.5 mM glucose, 4.92 mM pyruvate and 5.39 mM fumarate, pH 7.4. The hearts were paced at 360 beats per minute. All hearts were equilibrated with Krebs Ringer bicarbonate buffer for 15 minutes prior to the experimental protocols described below. Hearts were subjected to either continuous flow for 45 minutes (control), 15 minutes no-flow ischemia, or 60 minutes no-flow ischemia with or without 45 minutes of reperfusion. No-flow ischemia was produced by wrapping the hearts in an impermeable plastic bag and submerging them in a water bath at 37° C. The left ventricular pressure was measured with a pressure transducer. Left ventricular pressures were 61.5±7.5 nm Hg during the 10 min equilibration period and 78.8±8.0 mm Hg after 45 min of perfusion. The pressure during reperfusion was 90.2±17.3 and 133.5±29.1 mm Hg following 15 min of ischemia and 60 min of ischemia, respectively.

Tissue and Effluent Sample Preparation

Fractions were collected at the end of the equilibration period. During reperfusion and the 45 minutes of perfusion (control), fractions were collected either every minute for 10 minutes, then every three minutes for the remainder of the protocol, or as entire effluent samples. The fractions were frozen immediately at −70 to −80° C. and then stored frozen or lyophilized. The left ventricles were frozen in liquid nitrogen and stored at −70° C. until analyzed.

SDS-PAGE and Western Blot Analysis of Tissue and Effluent Samples

Left ventricular tissue samples following Langendorf perfusion were skinned in 50% (v/v) glycerol and relaxing buffer containing protease inhibitor cocktail. The myofibrils from the global ischemia model and the left ventricular tissue were homogenized in 160 mM Tris, pH 8.8 plus the protease inhibitor cocktail. The protein content of the homogenate was determined using the Lowry assay. Homogenized samples were diluted two-fold with sample buffer consisting of 2% SDS, 5 mM Tris, pH 6.5, 20% sucrose, 0.05% bromophenol blue and 1 mM β-mercaptoethanol. Effluent samples used for SDS PAGE analysis were dialyzed against 1 mM hydrochloric acid, 1 mM β-mercaptoethanol with dialysis bags having a molecular weight cut off of 6000 daltons. The samples were then freeze-dried and taken up into 50 μl of 160 mM Tris, pH 8.8 plus the protease inhibitor cocktail and diluted two fold with gel dissolving buffer. Tissue samples (30 μg of total protein) and effluent samples (20 μg of total protein) were loaded on a 12.5% SDS polyacrylamide gel using a Hoeffer (Baie D'Urfe, Canada) or Biorad (Hercules, Calif.) mini-gel apparatus. Homogenized tissue samples, effluent samples, and RP-HPLC peaks collected from the affinity columns (see below) were separated by 12.5% SDS-PAGE, or by a modified tricine-SDS-PAGE system (T-PAGE) (Schagger et al. 1987, *Anal. Biochem.* 166:368-79) using the Mini-gel system (Biorad). T-PAGE was performed with a 10% T (total acrylamide concentration), 3% C (concentration of bis-acrylamide) resolving gel and 4% T, 3% C stacking gel, containing 6 M urea, 0.1% SDS, 1 M Tris-HCl, pH 8.45 (urea T-PAGE). The cathode running buffer consisted of 0.1 mol/l Tris-HCl pH 8.25, 0.1 mol/l tricine, 0.1% SDS, and the anode buffer consisted of 0.2 mol/l Tris-HCl pH 8.9. Samples were diluted 2 fold with sample buffer containing 2% SDS, 5 mmol/l Tris-HCl, pH 6.5, 20% sucrose, 0.05% bromophenol blue, with 100 mmol/l β-mercaptoethanol (β-ME) for SDS-PAGE, or with 6 mol/l urea and 100 mmol/l β-ME for urea T-PAGE. Samples were boiled for 5 min, loaded onto the gel, and run at 105 V for 1 to 1.5 h. Gels were transferred to nitrocellulose or PUDF using a wet transfer apparatus (Biorad) with 10 mmol/l 3-cyclohexylamino-1-propanesulfonic acid (CAPS), pH 11.0 for 16 h at 27 mA or 60 min at 100 V, at 4° C., or stained with Coomassie Blue and silver (Coligan et al. 1995, *Current protocols in protein science*. John Wiley & Sons, New York). Proteins were quantified on the stained gel or western blot by densitometric scanning using an Ultrascan XL enhanced Laser densitometer (Pharmacia LKB Biotechnology, Uppsala, Sweden) or by Corel Photohouse (version 8).

Figure 8:
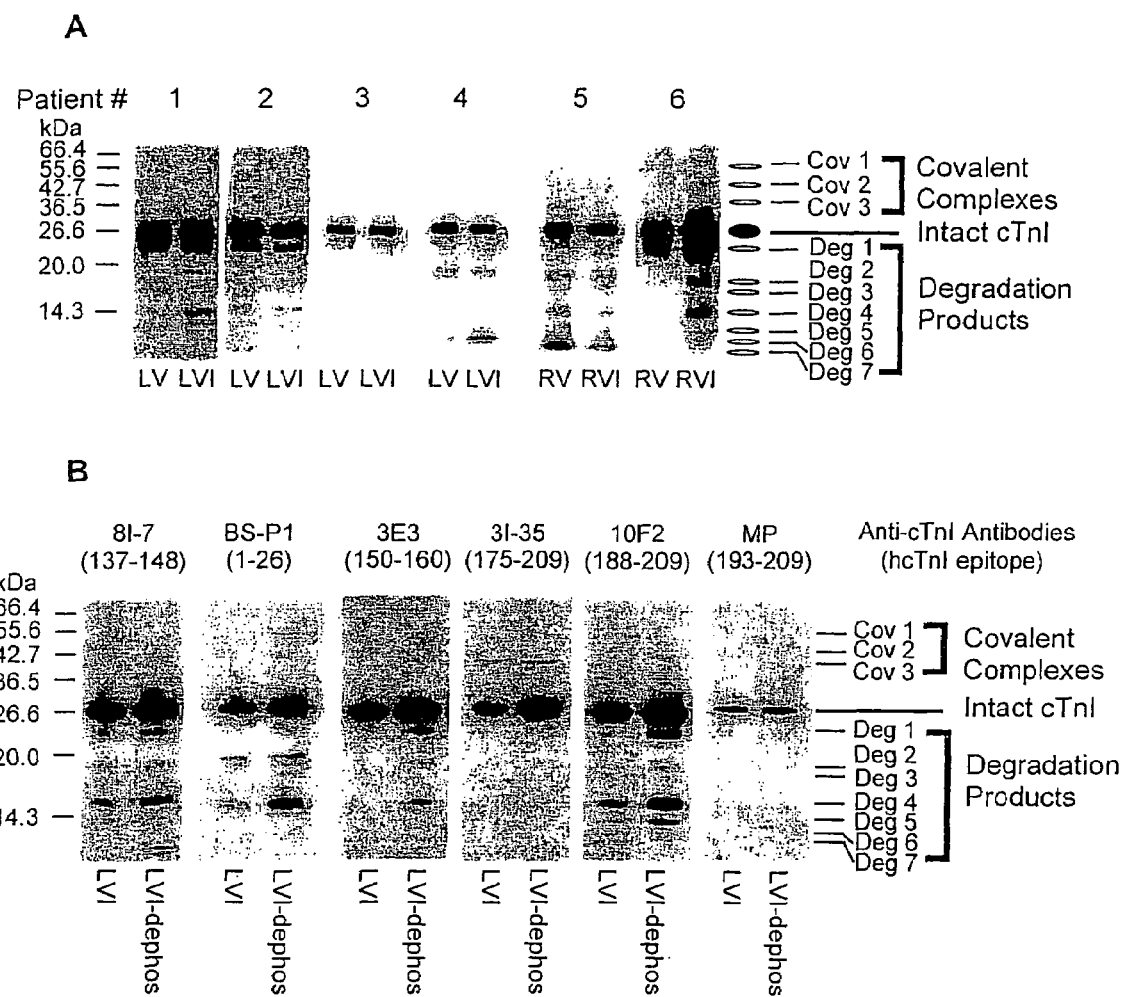
FIG. 8A shows anti-cTnI antibody (8I-7) western blots of 12.5% SDS-PAGE with 3 mol/L urea separated myocardial biopsies from representative patients, and a schematic of the protein-protein complexes and degradation products observed. Biopsies were taken from the left and right ventricle, before the application (LV, RV) and 10 minutes after the removal of the aortic cross-clamp (LVI, RVI).
FIG. 8B shows serial western blots performed with anti-TnI antibodies of various epitopes on hcTnI, defined by the residues on hcTnI with which they are known to interact. Each product has differential affinity for the various antibodies depending on the extent of modification. Note that at least one protein-protein complex exists which does not contain cTnI (see 4d-11).

Western blot analysis was done according to Van Eyk et al. 1998 (*Circ. Res.* 82.261-71) or else the primary antibodies were detected with goat anti-mouse IgG conjugated to alkaline phosphatase (Jandel Scientific) and CDP-Star chemiluminescence reagent (NEN-Mandel). The monoclonal antibodies used were anti-TnT clone JLT-12 (Sigma Chemical Co., St Louis, Mo.), anti-α-actinin clone EA-53, (Sigma) or anti-α-actinin clone 157 (provided by Spectral Diagnostics, Toronto, Canada), anti-MLC1 (provided by Abbott Laboratories, Chicago, Ill.) which recognizes amino acid residues 70 to 75, anti-TM (Sigma), anti-sarcomeric actin (Sigma), and anti-glyceraldehyde phosphate dehydrogenase (Cedarline Lab. Ltd, Canada). Several different anti-TnI antibodies were utilized: anti-TnI clone 3309 which recognizes amino acid residues 157 to 192 and clone AM-NI which recognizes TnI residues 1 to 65 (provided by Dr. J. Ladenson, Washington University St Louis, Mo.); P1 (Biospacific Inc.), an anti-peptide antibody to residue 1-26 of cTnI (this antibody does not bind well to TnI phosphorylated at the N-terminus which occurs with PKA activation); P3 (Biospacific Inc.), an anti-peptide antibody to residues 26-56 of human cTnI; anti-TnI clone 10F2 (MAb 10F2) which recognizes amino acid residues 189 to 199 (see epitope map FIG. 8 in Van Eyk et al, 1998, *Circ. Res.* 82:261-71), antibody provided by Dr. C. Larue at Univ. Innsbruck Med. School, Austria; MAb C5 (Research Diagnostics, Flanders, NS); and our anti-TnI peptide (P143T) residues 137 to 148 (MAb E2). The production of the anti-TnI peptide monoclonal antibodies including MAb E2 has been described in Van Eyk et al. 1995 (*Prot. Sci.* 4:781-90). MAb E2 recognizes intact skeletal and cardiac TnI and cardiac TnI peptides containing amino acid residues 136 to 148 (data not shown). As well, anti-TnI antibodies MAb 81-7 and 31-35 (both Spectral Diagnostics, Toronto, Canada), and MAb C5 (Research Diagnostics, Flanders, NS), which recognize TnI amino acid residues (136 to 153, 188 to 199, and 188 to 199, respectively, see McDonough et al. 1998, *Biophysical J* 74:A354).

Epitope mapping of these various antibodies was carried out by 12% SDS PAGE of intact cardiac TnI and various TnI fragments followed by western blot analysis as outlined above. Bovine cardiac TnI and rabbit skeletal TnI were purified by HPLC (Ingraham et al. 1988, *Biochemistry* 27:5891-98); recombinant rat cardiac TnI fragments 54 to 210, 1 to 188, and 1 to 199 were provided by Dr. A Martin (Univ. Illinois at Chicago, Chicago, Ill.; Rarick et al. 1997, *J. Biol. Chem.* 272:26887-92), and the synthetic skeletal TnI peptide 96 to 142, which is equivalent to the cardiac peptide residues 129 to 175, was prepared by solid-phase peptide synthesis (Tripet et al. 1997, *J. Mol. Biol.* 271:728-50). Human TnI fragments 1-153 and 154-210 were produced by CNBr digestion.

Figure 2:
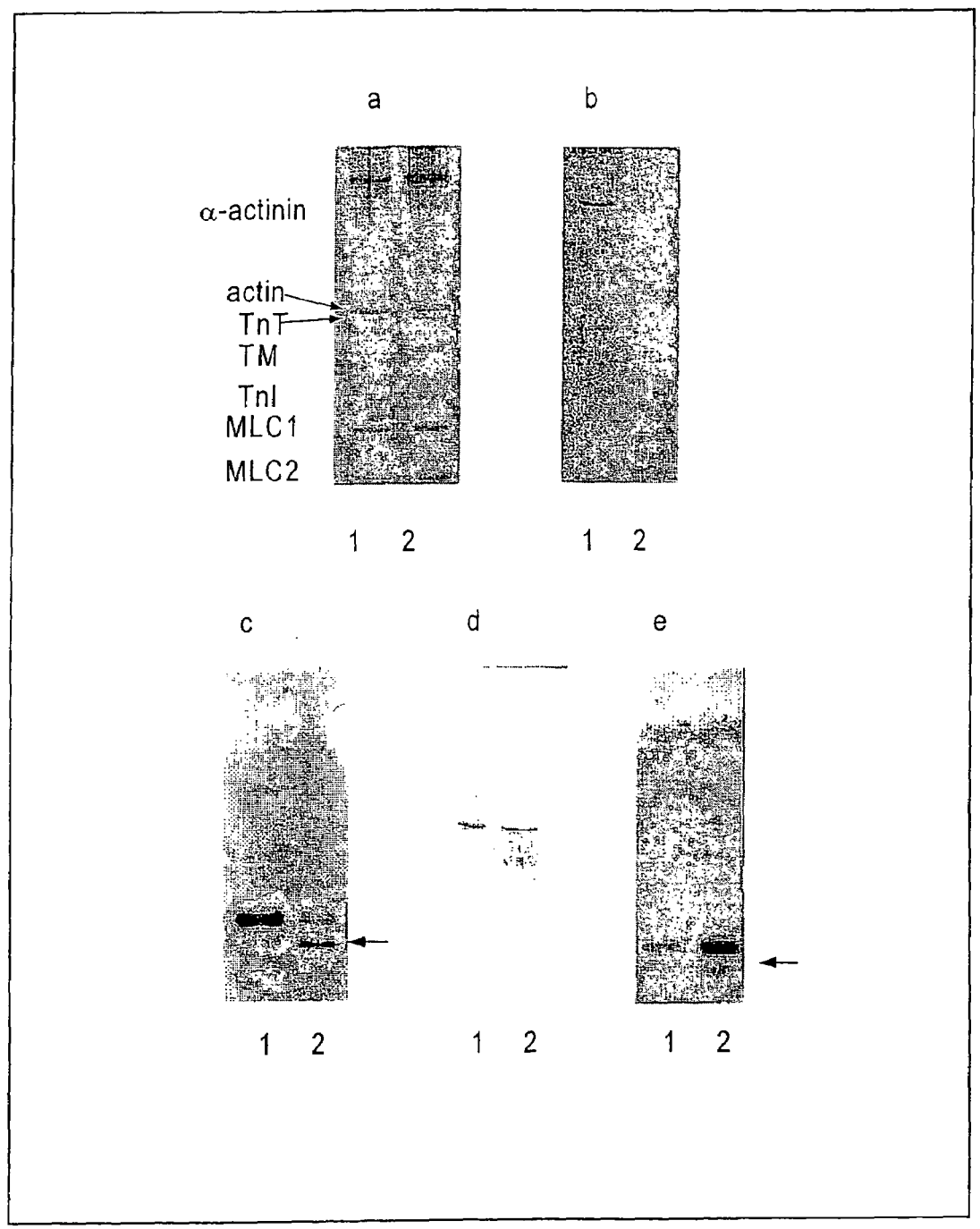
FIG. 2 shows the results of an SDS-PAGE analysis of isolated myofibrils from control and globally ischemic rat hearts. Left ventricular tissue samples obtained from isolated rat hearts were placed in saline in plastic bags for 60 min at either 4° C. (control, 1) or 39° C. (global ischemia, 2). Panel A shows the coomassie blue stain of the 12.5% crosslinked gel. Panels B to F show corresponding western blots using anti-a-actinin (panel B), anti-TnI peptide residues 136 to 148 (panel C), anti-TnT (panel D), and anti-MLC1 (panel E) antibodies. Modification products are indicated by arrows. The data reveal a loss of α-actinin in the global ischemic myofibrils.
Figure 3:
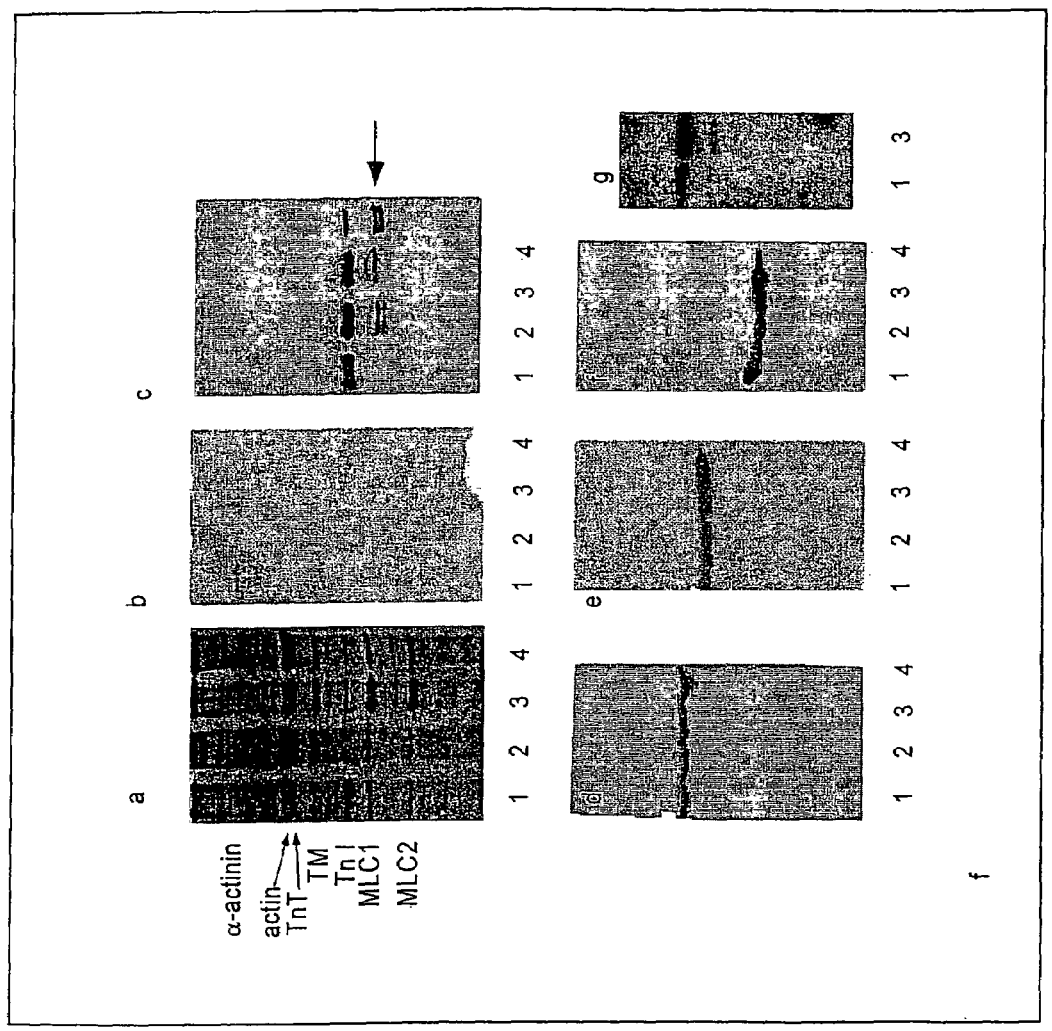
FIG. 3 shows an SDS-PAGE analysis of skinned left ventricle tissue samples from isolated rat hearts after 15 min equilibration followed by either 45 min perfusion (control, 1), 15 min ischemia followed by 45 min reperfusion (i.e., 15/45; 2), 60 min ischemia (3) or 60 min ischemia followed by 45 minutes reperfusion (i.e., 60/45; 4). Panel A shows the coomassie blue stain of the 12.5% crosslinked gel. Panels B-F show corresponding western blots using anti-a-actinin (panel B), anti-TnI peptide residues 136 to 148 (MAb E2, panel C), anti-TnT (panel D), anti-TM (panel E), and anti-MLC1 (panel F) antibodies. Panel G shows the western blot of a 10% SDS-PAGE of control tissue and tissue obtained from rats which experienced 60 min ischemia (2). The western blot was probed with anti-a-actinin antibody. Modification products are indicated by arrows.

Results of the SDS-PAGE analysis and subsequent western blots of rat heart reperfusion effluent are shown in FIG. 1, and of tissue from global ischemic rat hearts in FIG. 2, wherein MLC1 modification product is identified by an arrow. FIG. 1D shows a that a 32 kDa protein-protein complex is formed from fragments of TnI, TnT, and TnC. FIG. 3 shows the SDS-PAGE analysis and subsequent western blots of rat skinned ventricular tissue, wherein TnI modification products can be seen (arrow). Note that -actinin was lost with mild ischemia, and -actinin degradation appeared with more severe ischemia.

We note that C5 does not bind to TnI that has an ischemia-induced modification. This specific site is therefore novel. As well, 2I-14 Mab (Spectral Diagnostics) which recognizes amino acid residues 80-153 of human cTnI does not bind to phosphorylated TnI. This phosphoryalion site is ischemia-induced and must be amino acid residues 122, 125 or 142. The first two residues are unique sites and thus involve a new unidentified kinase.

Amino Acid Sequencing of Tissue and Effluent Samples

Figure 4:
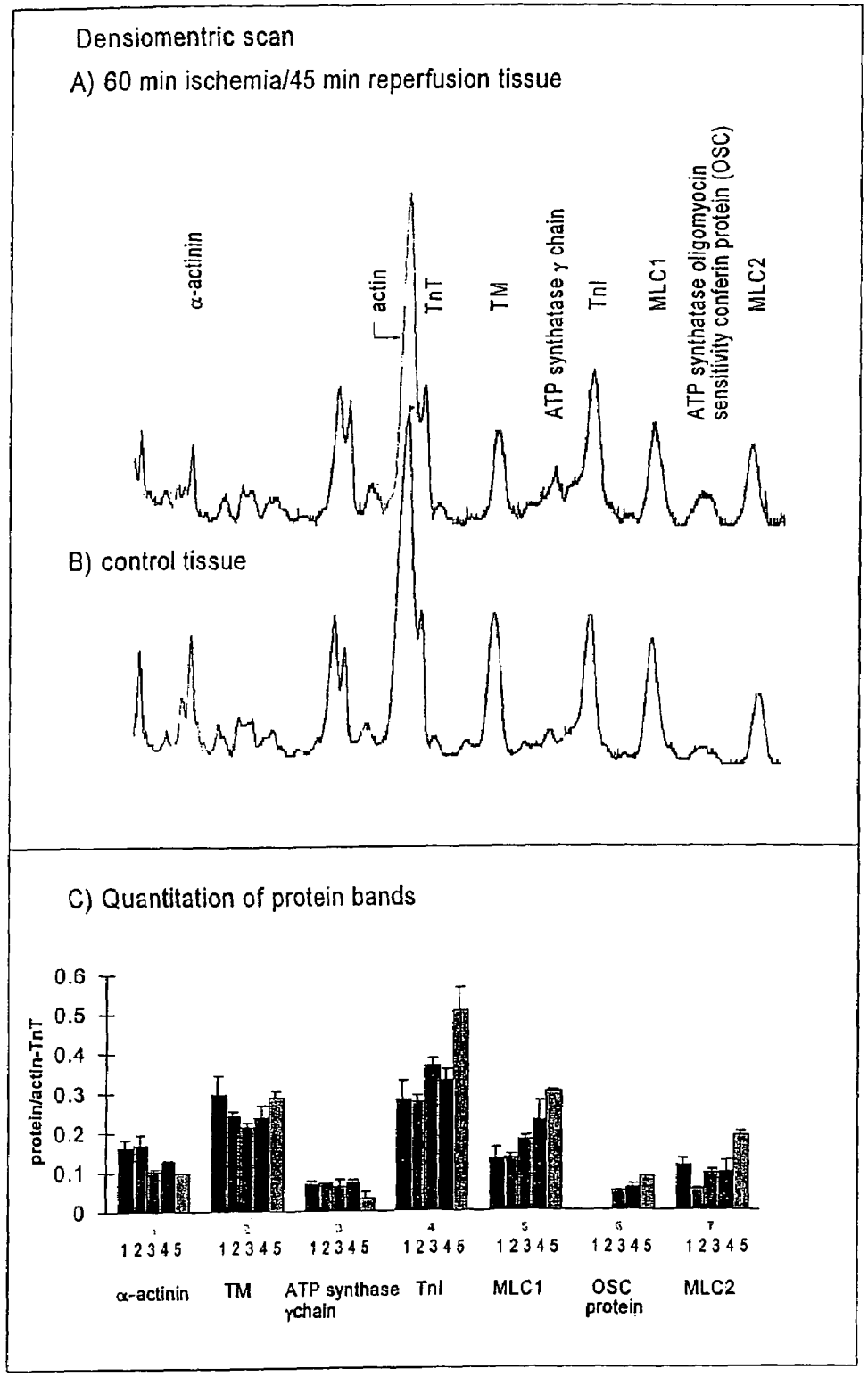
FIG. 4 shows densitometry scans of SDS-PAGE runs of rat skinned left ventricular tissue samples. Panels A and B show densitometric scans of a 12.5% SDS-PAGE of tissue from rat hearts that experienced 15 min equilibration followed by either 45 min perfusion (control, panel B) or 60 min ischemia followed by 45 min reperfusion (60/45, panel A). Panel C shows the quantity of protein at each corresponding peak of the densiometric scan. Tissue samples from 4 to 6 rats were analyzed for each of the following conditions: 45 min perfusion (control, lane 1), 15 min ischemia (lane 2), 15 min ischemia followed by 45 min reperfusion (15/45, lane 3), 60 min ischemia (lane 4) and 60 min ischemia followed by 45 min reperfusion (60/45, lane 5). 30 μg of total protein were loaded on each gel lane. Variation in the amounts loaded was taken into account by standardizing the quantity of each peak with respect to the quantity of TnT-actin peak.
Figure 5:
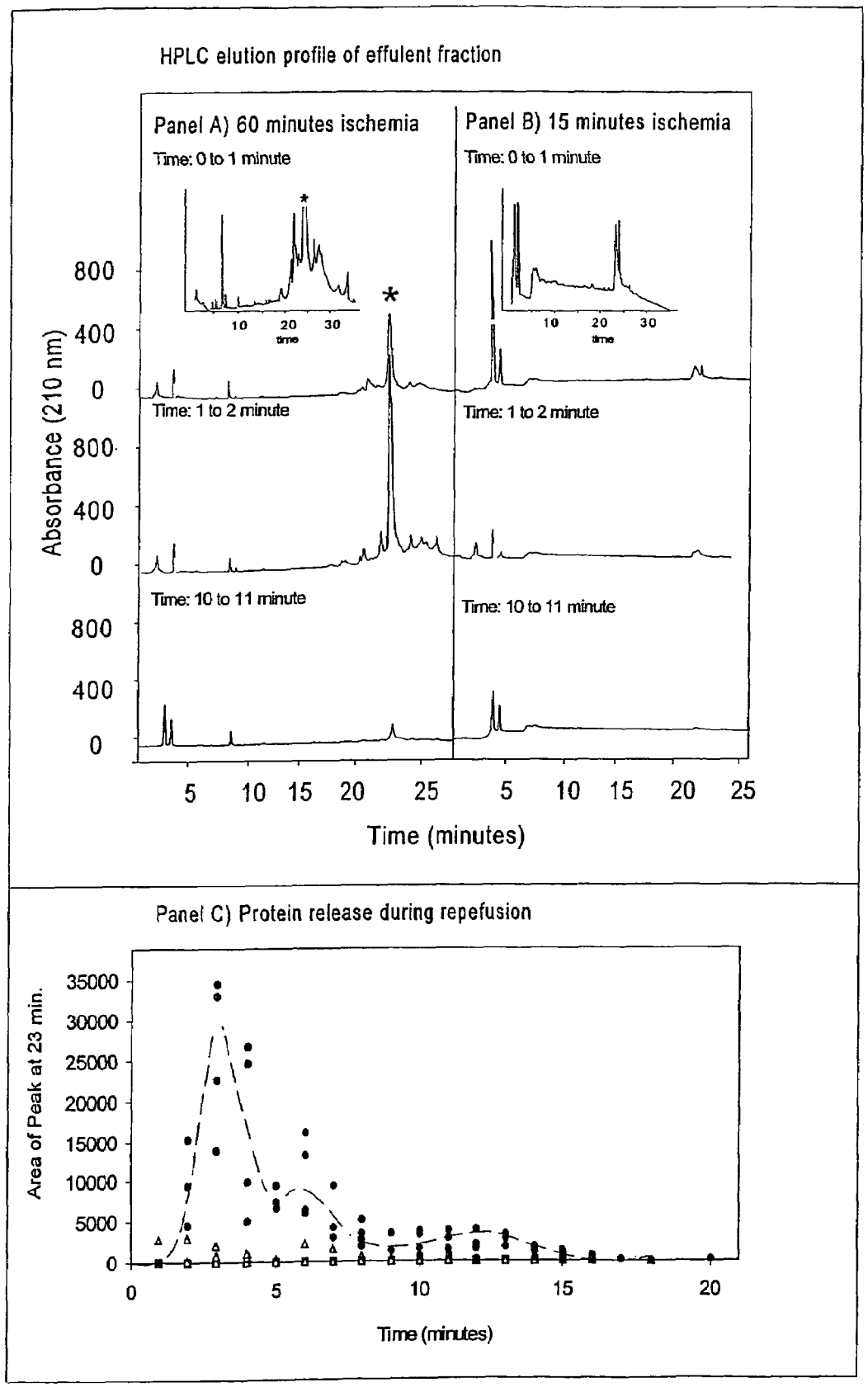
FIG. 5 shows the results of a reversed-phase high performance liquid chromatographic (RP-HPLC) analysis of proteins present in the reperfusion effluent following release from the isolated ischemic rat heart (N=4 to 6 per experiment). Panel A and B inserts show enlarged scale (−20 to 200 milliabsorbance units) of the elution profile of the initial one minute fraction following 60 min ischemia Injection peak occurs at 6 min and the peak eluted at 23 min (*) was integrated to determine its peak area. The peak area reflects the amount of protein present in the effluent at that time point. Panel C shows the area of the peak eluted at 23 min for each fraction collected during the reperfusion. Circles, 60 min of ischemia; triangles, following 15 min of ischemia; squares (control), perfusion with no ischemia.

Tissue and effluent samples were prepared and electrophoresed on a 12.5% SDS polyacrylamide gel as described above. The proteins were transferred onto a polyvinyline difluoride protein sequencing membrane (PVDF, Biorad) using 10 mM 3-(cyclohexylamino)-1-propanesulfonic acid buffer (Matsudaira et al. 1987, *J. Biol. Chem.* 262:10035-41) at 100 mA for 55 min using a Biorad mini-transfer system. A Hewlett Packard G1005A protein sequencer was used to sequence the initial amino acids of selected bands from the PVDF membrane using standard procedures (Alberta Peptide Institute, Edmonton, Canada). Table 1 and FIG. 4 show the results from this assay which indicate that other proteins, including malate dehydrogenase, ATP synthase r subunit, and OSC, are also present in all ischemic tissue samples. Further, cellular proteins such as myofilament proteins and others such as triose phosphate isomerase (FIG. 1) are present in the effluent.

HPLC Analysis of Effluent

The lyophilized effluent fractions from isolated rat hearts were dissolved in 1 ml of water for every min of perfusion. HPLC analysis of the effluent was performed on an analytical Zorbax C8 300SB reversed-phase column (4.6 mm I.D.×250 mm). The HLPC system consisted of a Hewlett Packard series 1090 LC coupled to a Hewlett Packard Vectra 486 166 MHz XM processor or Varian HPLC system comprising a 9100 autosampler, a 9012 solvent delivery system, and a 9065 polychromatograph. The proteins were eluted using an A/B buffer system. Buffer A was composed of 0.05% trifluoroacetic acid and buffer B of 0.05% trifluoroacetic acid in acetonitrile. The gradient consisted of an isocratic hold (100% A) for 5 min followed by a 2% B linear gradient at 1 ml/min. The proteins and protein fragments were monitored at an optical density of 210 nm or 278 nm. The quantity of protein present in each effluent fraction was estimated by determining the area of the peak eluted at 23 min. We have previously shown that peak area is directly related to the quantity of protein present (see Van Eyk et al. 1997, *J. Biol. Chem.* 272:10529-10537). This method of quantification assumes that the same protein(s) is eluted at 23 min in the various effluent fractions from the different protocols. FIG. 2 shows representative protein elution profiles of these fractions for the 0, 1 and 10 min samples following 60 (panel A) or 15 (panel B) min of ischemia. The inset shows an enlarged scale of the 0 to 1 min fraction. These results indicate that, compared to 15 min ischemia, the 60 min ischemic episode resulted in release of many more different proteins and protein fragments. These results indicate that loss of cellular membrane integrity occurs after 15 min ischemia.

EXAMPLE II

Detection and Characterization of TnI Modification Products

Serum

Serum was obtained from 12 patients admitted to the Kinston General Hospital emergency department with suspected MI, and kept frozen until use. All patients analyzed had definitive diagnosis of AMI. CKMB was measured on receipt of each sample using the Technicon Immuno 1 (Bayer Corporation, Tarrytown, N.Y.). Under clinical conditions, CKMB is considered negative for MI if the absolute mass is less than 8 mg/L. The proteolytic susceptibility of TnI and TnT in scrum was determined by addition of recombinant human cardiac TnI and TnT obtained from Spectral Diagnostics (Toronto, Canada) to normal control human serum to a final concentration of 500 ug/L at 37° C. for up to 52 hours. As little as 1 ug/L can be detected.

Electrophoresis and Western Blot Analysis

Figure 7:
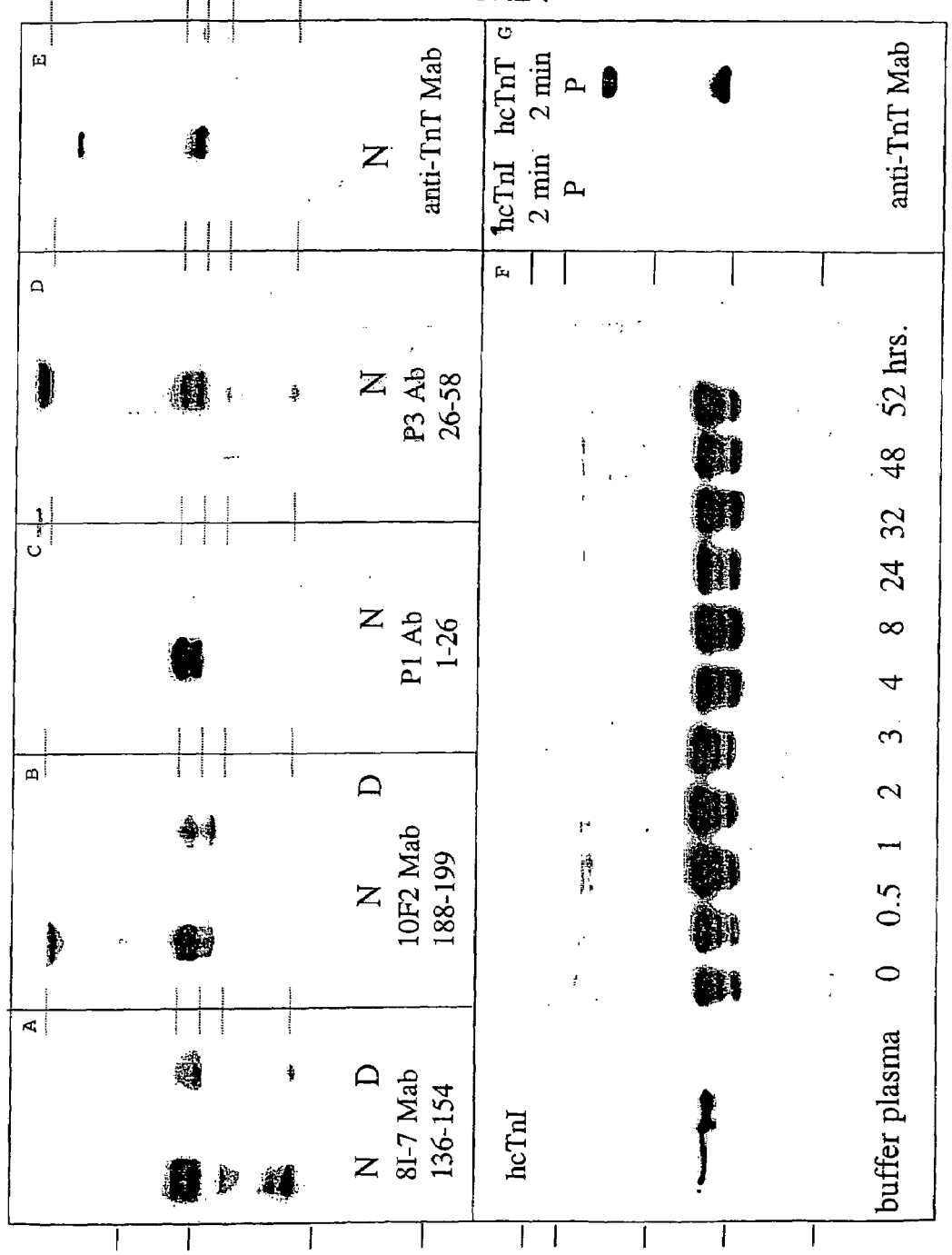
FIG. 7 shows characterization of serum TnI modification products with western blot analysis using several anti-TnI antibodies to different epitopes on TnI panels A-F) or an anti-TnT antibody (panel I) of serum from patient #2 at time of admission into the emergency room (the time of maximum change). Native serum (N), serum obtained directly from patient or dephosphorylated (D) using alkaline phosphatase treatment were analyzed.

Plasma from MI patients or control plasma spiked with hcTnI or hcTnT was diluted in sample buffer containing 0.33% SDS, 0.33% CHAPS, 0.33% NP-40, 0.1 M DTT, 8 M urea, and 50 mM Tris, pH 6.8 in 50% glycerol. Samples were boiled for 10 min. 25 µl of sample (equivalent to 2 µl of plasma) was loaded on 12% SDS PAGE. After gel electrophoresis proteins were transferred onto nitrocellulose (Micton Separation Inc., Westborough, Mass.) in 10 mM CAPS, pH 11.0 for 1 hour at 100 V at 4° C. Anti-TnI antibodies used were as follows: 0.35-0.75 g/ml of 81-7 Mab (epitope residues 136-154, Spectral Diagnostics Inc., Toronto, Canada); 0.5 µg/ml of a polyclonal antibody either peptide 1 (epitope residues 1-26) or peptide 3 (epitope residues 26-58, both Biospacific, Meryville, Calif.); and 0.25 µg/ml of 10-F2 Mab (epitope residues 188-199, Sanofi Diagnostics Pasteur, Marnes-LA-Coquette, France). For TnT, an anti-cTnT peptide polyclonal antibody (epitope residues 3-15 (recognizes all isoforms), Biospacific, Meryville, Calif.) was used at 0.5 µg/ml. The specificity of this antibody for TnT was determined against purified recombinant human cTnI and the antibody did not cross-react with any serum proteins, as seen in plasma spiked with TnI (FIG. 7, panel G). Anti-mouse or goat secondary antibodies conjugated to HRP (Jackson Laboratories, West Grove, PN) and chemiluminase (Boehringer Mannheim, Québec, Canada) was used for detection.

Protein Dephosphorylation

Serum was diluted 2 fold in assay buffer consisting of 50 mM Tris pH 7.5 and 1 mM magnesium chloride. Tissue homogenate or diluted serum was added to 20-30 units (1 unit hydrolyzes 1 nmole of PNPP/min at 30° C. pH 8.5) of alkaline phosphatase conjugated agarose beads (Simga) are prewashed with assay buffer three times prior to adding of 100 µl of serum. Serum or tissue homogenate and AP-beads are incubated at 37° C. for 30 min. Supernatant was removed after centrifugation at 16,000×g and stored at −70° C. until analyzed.

2-D Gel Electrophoresis

The first dimensional separation of proteins, from whole tissue homogenates, was performed either in IPG strips or slab IEF gels. IPG strips pH 4-7 and pH 7-10 (linear gradient) (Protean IEF cell, Bio-Rad) were rehydrated in the presence of protein sample in rehydration buffer (8M urea, 2% (w/v) CHAPS, 0.5% Bio-Lyte 3/10 Ampholyte, 15 mM DTT, 1% bromophenol blue) at 50 V for 12 h. Focusing was conducted for a total of 25000 Vh, 5.1% polyacrylamide slab JEF gels were prepared using different combination of narrow and broad range ampholytes (Bio-Rad) and focused at 400 V for 5 h. Slab IEF gels done using in 6 M urea, 2.4% ampholytes and 20 mM NaOH. Proteins were resolved on a mini-Protean I (Biorad) electrophoresis apparatus using a 10 well comb with an ampholyte mixture of 70% pH 3.5-10 (Sigma) and 30% pH 8.5-10 (Pharmalite). The gels were prerun at 200 V for 10 min, 300 V for 10 min followed by 400 V for 60 min. The individual lanes were cut and placed on top of the second dimension gel following equilibration in Tris-glycine buffer.

The second dimension separation for both type of first dimension gels was performed in 12 or 15% resolving, 4.5% stacking gel by SDS-PAGE. The proteins from the gels were either silver stained or transferred to nitrocellulose membrane for immunoblot analysis.

Results and Discussion

Figure 6:
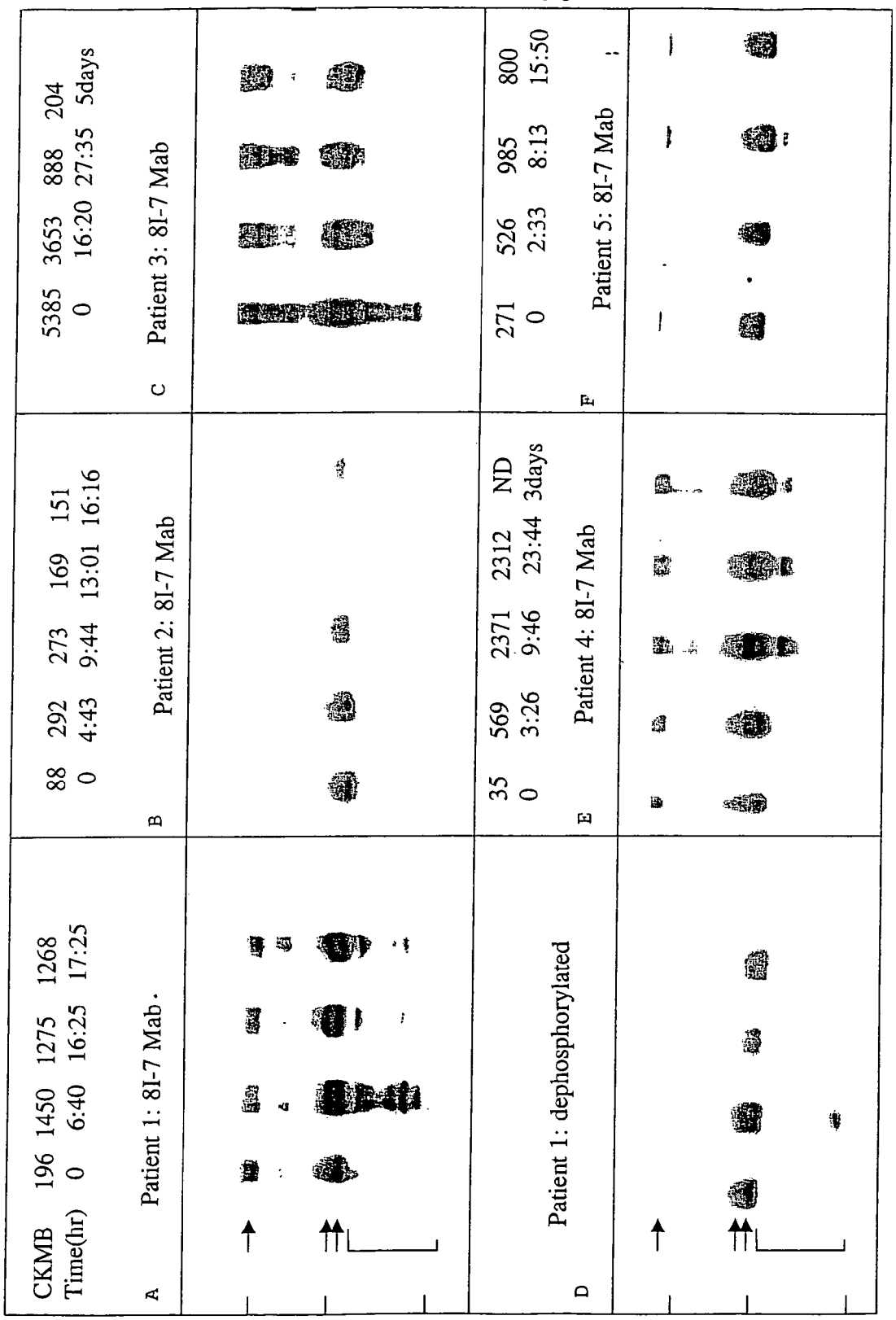
FIG. 6 shows a western blot analysis of cardiac TnI in serum from five patients with myocardial infarction, showing that modification of TnI changes in quantity and extent over time since MI.

In addition to intact TnI, there was a multitude of modification products: a) up to 8 degradation products were observed in the serum from different patients; and b) high molecular weight products were also observed (FIG. 6). Furthermore, TnI and its modification products were phosphorylated as seen by comparing the western blot of 4 blood sera obtained from patient 1 with the same samples dephosphorylated with alkaline phosphatase FIGS. 6 A and D, respectively). In fact, the results suggest that phosphorylated TnI is one of the initial species (compare FIGS. 6 A and D and FIG. 7 A), but whether it is the first species cannot be determined since it was known how advanced the MI of each patient was. However, the results clearly demonstrate the presence of large quantities of phosphorylated TnT in serum of MI patients, which has never been shown previously.

It is important to note that the numbers and types of modification products present in the serum varied with the time the initial blood sample was taken, producing a continuum of changing TnI profiles. Even 5 days following MI, TnI and its modification products were detected in the blood (see patient 3 and 4, FIGS. 6 C and E). It has been documented using commercially available diagnostic MI kits that cardiac TnI and TnT can be detected in blood within 4 to 6 h following MI, and peak after 18 to 24 h, remaining elevated for up to 7 weeks. By western blot, the appearance of TnI degradation products is dependent on the severity of the infarction as judged by CKMB serum levels. In the time courses of the twelve patients analyzed, no small molecular weight TnI degradation products were detected in serum samples with CKMB levels below 1000. This suggests that in these patients TnI was degraded in the myocardium during severe acute MI. This is supported by a recent study that showed TnI in the majority of patients undergoing bypass surgery had TnI degradation in their myocardium before and/or after surgery (McDonough et al., soon to be submitted). In bypass patients we have found that the quantity of several TnI degradation products in the myocardium correlates with the quantity of CKMB detected in the plasma and hence with the severity of injury.

Initial characterization of various TnI modification products observed in the serum of MI patients was accomplished by using several anti-TnI antibodies which recognize different regions of cardiac TnT (FIG. 7, panels A to D). C-terminal truncation occurs first as shown by the loss of immunoreactivity of the TnI degradation products observed when antibodies to the C-terminus are used in the western blot (FIG. 7, compare panels B and A). Furthermore, the time courses of patients with MI show that many patients have either intact TnI (phosphorylated and dephosphorylated) or intact with the N-terminus of TnI plus the one degradation product with the C-terminus proteolyzed (see FIG. 6). Only the lowest molecular weight degradation product is formed due to the cleavage of both the N- and C-terminus of TnI (FIG. 7). The invention thus furthers blood analysis by detecting TnI and its modification products, including phosphorylated forms, during the onset and development of MI with time.

EXAMPLE III

Myofilament Protein Alteration During Bypass Surgery

In this study coronary artery bypass surgery was used as a human model condition of ischemia/reperfusion injury. While not as severe an injury as myocardial infarction due to cardioprotective measures, this model provides an ischemic episode with both a defined time of onset (i.e., the application of the aortic cross-clamp), and a controlled length (i.e., the total cross-clamp time), as well as access to the myocardial tissue both before and after the ischemic episode. Through analysis of myocardial biopsy samples and serial serum samples for cTnI, we are able to demonstrate that: i) cTnI is modified in human myocardium both before and after the surgery; ii) the cTnI modification products can be characterized as C-terminally and/or N-terminally modified; iii) some of these modification products are eventually released into the serum; and iv) the extent of cTnI modification is related to both the surgical times and the length of hospital stay following the surgery. This indicates that for many patients the myocardium is already injured even though there is little TnI in the blood (not detected using commercially available kits but seen in our experiments by western blot). The pattern of degradation product and protein-protein complex formation (and expected phosphorylation status) of these patients' cardiac TnI prior to surgery is related to the stage of HF or extent of injury and provides an indication of their prognosis after surgery.

In addition, we present for the first time a western blot analysis of whole serum, and demonstrate the presence of both cTnI degradation products and cTnI containing protein-protein complexes in the serum both before and after the surgery. This is the first study to demonstrate that cTnI modification can occur in a human model condition of ischemia/reperfusion, that the modification is both selective and related to the duration of the ischemic episode, and that the specific cTnI modification products produced are predictors of clinical outcome.

Methods

Forty patients who underwent elective coronary bypass at Kingston General Hospital were recruited to participate in this study between June 1998 and February 1999. The Human Research Ethics Board of Queen's University approved this study, and all patients gave informed consent. Exclusion criteria included age under 21 or over 75, and those with congenital heart defects or valvular heart disease. Three patients were excluded: one on the basis of age, one because a modified surgical technique had to be used, and one due to missing clinical data.

Surgical Technique and Myocardial Protection

Patients underwent multiple coronary artery bypass grafts with use of the internal mammary artery and saphenous vein grafts. A single cross-clamp technique on full cardiopulmonary bypass with a flow rate averaging 5 to 6 LPM and perfusion pressure 50 to 70 mmHg was performed. Cardioplegic solutions consisted of: (High K) Plasmalyte 56 with 5% dextrose, 50 mM $NaHCO_3$, 50 mM KCl, 200 mg lidocaine; or (Low K) Plasmalyte 56 with 5% dextrose, 50 mM $NaHCO_3$, 6 mM KCl, 50 mg lidocaine. Cardioplegic solution was infused through a 14 gauge angio catheter inserted into the proximal ascending aorta after placement of the aortic cross-clamp. A standard cardioplegic infusion set was used with a mix of crystalloid solution and blood from the arterial circuit at a ratio of 4:1. Warm blood cardioplegia (High K only) was infused at 37° C. with an initial bolus of 600 mL followed by intermittent boluses of 400 mL after completion of each proximal vein anastomosis (n=14). Cold blood cardioplegia was infused at 4° C. with an initial bolus of 1000 mL (High K) followed by intermittent boluses of 250 mL (High K) after each proximal anastomosis was completed (n=26). On completion of the mammary anastomosis, a 'hot-shot' of 400 mL (Low K) at 37° C. was infused into the aorta prior to removal of the cross clamp. No differences in any parameters, including serum CKMB and cTnI degradation products 1, 2, and 4, were noted between the two cardioplegic methodologies. The patients were maintained at systemic normothermia in all cases. Standard anaesthetic techniques including high dose fentanyl anaesthetic supplemented by forane (inhalant or CPB circuit) and neuromuscular blocking agent were used. Cardiopulmonary bypass was maintained using moderate hemodilution (hematocrit 20-25), with a centrifugal pump and membrane oxygenator via single arterial and venous (two stage) cannulae. Heparinization and reversal with protamine were employed in the conventional method. Median sternotomy and vein harvest simultaneous with mammary harvest followed by grafting on pump were performed in the usual fashion. Serial ECG's pre and post operatively were assessed and the diagnosis of MI was made based on new Q wave or loss of R wave.

Tissue and Blood Sampling

Left and right ventricular (LV and RV) subcardial biopsy samples (~50-100 μg) were obtained after initiation of bypass prior to clamping, and 10 minutes after removal of the cross clamp. Samples were taken from the anterior or inferior RV and the anterolateral LV where there was good muscle and no visible scar, without obscuration by epicardial fat. No complications resulted from biopsies. The biopsy samples were frozen immediately in liquid nitrogen in the operating room and stored at −70° C. until biochemical analysis.

Serial blood samples (5 mL) were analysed at the Kingston General Hospital laboratories for serum CKMB and TnI (after initiation of bypass prior to clamping (time=0), 10, and 30 minutes, and 3, 24, and 72 hours following cross-clamp removal). cTnI measurements were performed on the ACCESS immunoassay system (Sanofi Diagnostics Pastcur S.A, Mames-la-Coquette, France). CKMB measurements were performed on the Technicon Immunol (Bayer Corporation, Tarrytown N.Y., USA). Aliquots of serum were retained and frozen at −70° C. for further analysis.

Electrophoresis and Western Blotting

Biopsy samples were homogenized in 25 μL of homogenization buffer (100 mmol/L Tris-HCl, pH 6.8, 6 mol/L urea, 3.6 μmol/L leupeptin, 2.1 μmol/L pepstatin A, and 50 μmol/L phenylmethylsulfonylfluoride), boiled, added to an equal volume of sodium dodecyl sulfate-polyacrylamide gel electrophoresis (SDS-PAGE) sample buffer (200 mmol/L Tris-HCl, 2% SDS, 20 mmol/L dithiothreitol (DTT), and 0.05% bromophenol blue, pH 6.8), and loaded onto 12.5% SDS-PAGE gels (with 3 mol/L urea), and electrophoresed for 1 hour at 105 V on a Mini-gel system (BioRad). The small sample size precluded protein measurements. Serum samples (2 μL) were diluted 1.2 in PBS (to give 4 μL), and added to 16 μL of $H_2O$, 5 μL of modified sample buffer (165 mg SDS, 165 mg CHAPS, 165 uL NP-40, 250 mmol/L Tris-HCl, pH 6.8, 50% glycerol, and 500 mmol/L DTT), and 1 kernel of urea (to give a final concentration=3 mol/L), and boiled. The serum samples were run on a 0.75 mm thick, 14 cm×17 cm 12% SDS-PAGE resolving gel with a 4% stacking gel, at 90V for 5.5 hours. The proteins from both tissue mini-gels and serum gels were then transferred to nitrocellulose at 27 V for 16 hours in 10 mmol/L 3-cyclohexylamino-1-propanesulfonic acid (CAPS), pH 11.0. Western blots were performed according to an established protocol (Van Eyk et al. 1995, *Protein Sci.* 4:781-790) on the transferred proteins using the monoclonal anti-TnI antibody 81-7 (Spectral Diagnostics Inc., Toronto, Canada; epitope of hcTnT residues 136-154). Serial western blots were performed on 3 samples with extensive modification using the following antibodies. BP-P1 and BP-P3 (BiosPacific, Emeryville, Calif.) are polyclonal anti-peptide antibodies raised against hcTnI residues 1-26 and 27-58 respectively. C5 (BioDesign, Kennebunk, Me.) is a monoclonal anti-hcTnI antibody the epitope of which has been mapped to the extreme C-terminus (residues 175-210, see methodology in Van Eyk et al. 1998, *Circ. Res.* 82:261-271). MP is a polyclonal anti-peptide antibody raised in our lab against hcTnI residues 193-209 (as per Van Eyk et al. 1995, *Protein Sci.* 4:781-790). A monoclonal anti-TnT antibody (BioDesign, Kennebunk, Me.) of unknown epitope was also used. The primary antibodies were detected using goat anti-mouse IgG conjugated to alkaline phosphatase (Jackson Immuno Research Laboratories) and CDP-Star chemiluminescence reagent (NEN-Mandel). The 81-7 western blots were quantified within the linear range as previously described (McDonough et al. 1999, *Circ. Res.* 84:9-20), with the TnI products in each sample expressed as a percentage of the total amount of TnI in the sample. The samples were randomized following scanning, and the code only broken once the quantification was completed. Multiple time exposures were used to quantify bands which constituted less than 5% of total TnI in the sample, while error in measurement was estimated at <2% based on repeated measurements of standard blots. The amount of each modified product, and the amount of total TnI, in each sample was used in a full statistical comparison with preoperative clinical variables (e.g. previous MI, drug therapies, age etc) and post-operative clinical outcomes (only those in hospital, approximately 5 days following surgery, including post-op MI, atrial fibrillation, ventricular fibrillation, etc.).

Statistical Analysis

Patients were categorized according to serum (1,2) and then tissue (A, B, C, D) groups (Table 2). Univariate statistics (percentages, means and standard errors, as appropriate) were used to describe the patient population by surgical outcomes, demographic characteristics, and the presence of salient, pre-existing medical conditions. Graphical analysis were used to profile the release of CKMB and cTnI into the serum of patients before application of the cross clamp, and at the following times after cross clamp removal: 0.2, 0.5, 3, 24, and 72 hours. Twenty-four hour serum levels of CKMB and cTnI were compared between the two serum groups, as were the relative levels of intact cTnI and individual degradation products 1, 2, and 4 present in the myocardium of patients in the two serum groups. A second graphical analysis and statistical comparison was used to profile and compare the release of CKMB and cTnI in the serum of patients in the four tissue groups. Levels of the three degradation products in the myocardium of patients in tissue groups A, B, C, and D were also compared. Non-parametric statistics (Mann-Whitney U-tests) were used in all of these statistical comparisons.

Bypass, cross-clamp, and reperfusion times were compared between groups of patients categorized by degradation products and tissue group. These three surgical outcomes and length of hospital stay were compared between patients categorized according to the two serum groups. Mann-Whitney U-tests were also used in these comparisons.

The abilities of specific degradation products to correctly indicate the presence or absence of pre-existing disease (MI, Class IV Angina, Diabetes) were described according to their sensitivity and specificity. Fisher's exact test was used to calculate the statistical significance of associations between the appearance of these degradation products and the presence/absence of these preexisting conditions. Similar calculations were performed to determine the association between the tissue degradation product groups (A, B, C, D) and the presence of significant myocardial damage (serum CKMB>8 ng/mL) at 24 hours after cross-clamp removal, as indicated by the serum groups (1, 2).

A. Selective Modification of Troponin I in Human Myocardium cTnI was selectively modified in human myocardium, both before the application of the aortic cross-clamp and following its removal, and the pattern of cTnI modification was complex (FIG. 8A). Western blots were performed using an anti-TnI antibody on biopsy samples obtained from the left and right ventricles before the application of the aortic cross-clamp (LV and RV), and 10 minutes following the removal of the cross-clamp (LVI and RVI)(FIG. 8A). A maximum of 3 protein-protein complexes (MW 60, 50, and 40 kDa; Cov 1 through Cov 3, respectively) and 7 degradation products (MW 23, 20, 16, 15, 12, 10, 9, 8 kDa; Deg 1 through Deg 7, respectively) were observed. Patients varied extensively in both the amount of each cTnI modification product, and the change in particular products from before to after removal of the cross-clamp. Across all patients, no consistent differences were detected in any cTnI modification product from before to after removal of the cross-clamp, however this is likely due to different patterns of modification between patients, the relatively small sample size (n=37), and the heterogeneity of the disease states. The most abundant and frequently observed modification products were degradation products 1, 2, and 4 (Deg 1, Deg 2, and Deg 4), which correspond to molecular weights of 23, 20, and 15 kDa respectively (apparent molecular weight on 12.5% SDS-PAGE with 3 mol/L urea, intact hcTnI migrates at 26 kDa, see schematic in FIG. 8A).

B. Characterization of cTnI Modification Products

The cTnI modification products found in isolated rat heart models have been previously demonstrated to be the result of specific and selective C-terminal and N-terminal proteolysis, and non-disulfide covalent cross-links, with the primary 22 kDa degradation product identified as cTnI residues 1-193, resulting from proteolytic cleavage of 17 C-terminal amino acids. To determine if ischemia/reperfusion injury in human myocardium results in activation of similar processes, we performed serial western blots using anti-cTnI antibodies of various epitopes on LVI biopsy samples (FIG. 8B). It is important to note that modification, and subsequent lack of antibody interaction, may be a result of either degradation or phosphorylation, or some combination of these two processes. In particular, known protein kinase A and protein kinase C sites are found in the extreme N-terminus of cTnI, and this phosphorylation is known to disrupt antibody-antigen interactions. We examined the role of phosphorylation by performing the serial western blot analysis on the same LVI biopsy sample dephosphorylated by alkaline phosphatase. All of the degradation products, Deg 1 through Deg 7, have a C-terminal truncation, shown as a lack of interaction with either MP or 3I-35. However, the strong interaction of 10F2 with dephosphorylated Deg 1, Deg 4, and Deg 5 suggests that there may also be a C-terminal phosphorylation event. The degradation products appear to also have modified N-termini, but to differing degrees. Dephosphorylation significantly increases the response of Deg 1, Deg 2, and Deg 4 to BS-P1, which binds in the region known to be phosphorylated by PKA. Characterization of the individual modification products will require extensive further biochemical analysis.

C. Stratification of Patients Based on Serum CKMB

To examine the relationship between cTnI modification in the myocardium and post-operative patient outcome, patients were stratified in to one of two groups based on their serum CKMB levels at 24 hours following the removal of the aortic cross-clamp. As previously demonstrated by others (Sadony et al. 1998, *Eur. J. Cardiothorac. Surg.* 13:57-65; Bonnefoy et al. 1998, *Chest* 114:482-486), the patients in this study reach peak serum CKMB levels 12-24 hours following removal of the cross-clamp. It has also been shown that elevated serum CKMB at 12 or 24 hours following cross-clamp removal is prognostic for post-operative complications, including post-op MI (Sadony et al. 1998, *Eur. J. Cardiothorac. Surg.* 13:57-65; Bonnefoy et al. 1998, *Chest* 114:482-486). Based on these principles, patients were assigned one of two groups based on their 24 hour serum CKMB (Table 2) being either below (Group 1) or above (Group 2) the threshold for diagnosis of acute myocardial injury (CKMB>8 ng/mL). The CKMB and TnI release profiles for the two groups are shown in FIG. 9A. As expected, the timecourse of TnI release mirrors CKMB release, with the Group 2 being significantly elevated over Group 1 at 24 hours (p<0.05).

An anti-TnI antibody (8I-7) western blot of 12.5% SDS-PAGE (with 3 mol/L urea) separated serum samples from a Group 1 patient is shown in FIG. 9B. This is the first time that direct western blot analysis has been performed on whole serum. Surprisingly, cTnI was found in the serum before the cross-clamp, despite being below the detection limit for the diagnostic kit. While the serum cTnI measurements indicated below the western blot demonstrate a clear peak at 24 hours, the western blot does not appear to demonstrate the same magnitude of difference. However, the presence of modified cTnI, both degradation products and protein-protein complexes, throughout the timecourse suggests that the cTnI detection kit is not detecting all forms of cTnI in the serum. Whether these products are the result of release of modified cTnI from the myocardium, or the modification of released cTnI by the blood is not known.

The relationship between cTnI modification in the myocardium and serum CKMB levels for the two groups is shown in FIG. 9C. Patients with elevated CKMB (i.e. Group 2) had significantly less intact TnI, and significantly greater amounts of both Deg 1 and Deg 2 before cross-clamp, as compared to patients who did not have elevated CKMB (i.e. Group 1, $p<0.05$). Interestingly, there were no significant differences between the groups following cross-clamp removal, or in the right ventricle. This suggests that the presence of modified cTnI in the LV myocardium prior to surgery is likely to result in more extensive myocardial damage, and elevated release of CKMB and cTnI into serum following surgery.

D. Stratification of Patients based on cTnI Modification Profiles

Figure 10:
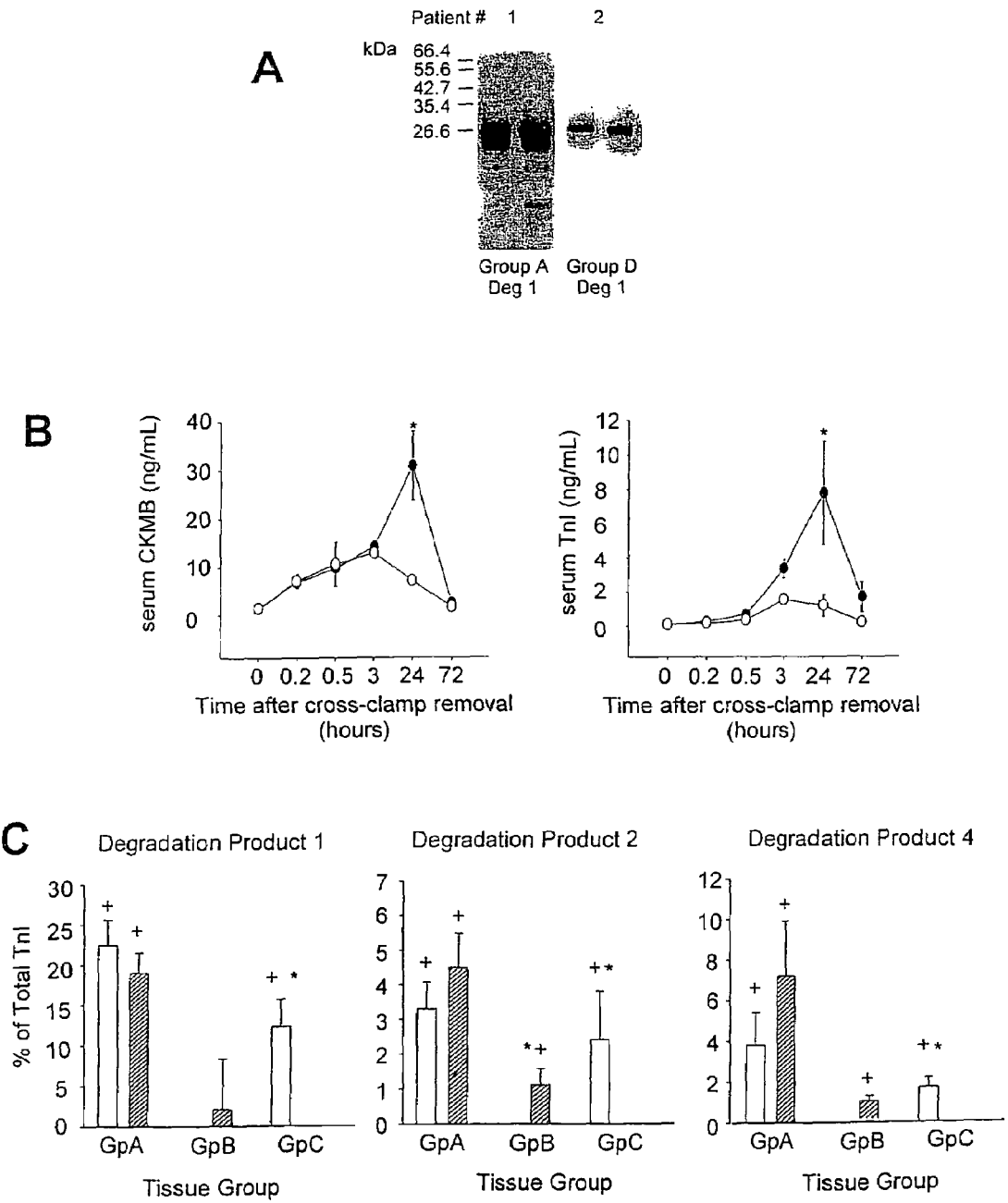
FIG. 10 shows stratification of patients by cTnI modification profile. Patients were assigned one of four groups on the basis of the presence and/or absence of each modification product before and after the cross-clamp (see Table 2).

To examine the clinical implications of cTnI modification in the myocardium, an analysis strategy was developed which took into account the different profiles of modification observed in myocardium, expressed as the presence or absence of each modification product, both before the cross-clamp and after its removal (Table 2). An example of how the grouping strategy was applied is shown in FIG. 10A. Patient 1 has degradation product 1 present both before and after cross-clamp, and therefore would be in Group A with respect to Deg 1. Patient 2 never has Deg 1, neither before or after cross-clamp, and so would be in Group D with respect to Deg 1. While these groups were formed using each patient with respect to each cTnI modification product, further analysis could only be performed for those cTnI products with sufficient numbers in each group to allow inter-group comparisons. The only products for which this type of analysis was performed were Deg 1, Deg 2, and Deg 4.

To determine if the presence or absence of specific cTnI modification products in the myocardium either before or after surgery is indicative of potential myocardial damage, the timecourses for serum CKMB and cTnI levels from before cross-clamp to 3 days following the removal of the cross-clamp were examined. Due to the size of the study, the analysis was limited to Deg 1 and Deg 2, since vast majority of products were not present in enough patients to warrant this type of analysis. The timecourses of serum CKMB and cTnI release for patients who had Deg 1 both before and after cross-clamp (Group A, n=18) and patients who never had Deg 1 (Group D, n=5) are shown in FIG. 10B. Group A demonstrates a significant elevation in both CKMB and cTnI over Group D at 24 hours following removal of the aortic cross-clamp ($p<0.05$). The same two groups with respect to degradation product 2 demonstrate similar profiles (data not shown, not significant). This implies that patients who had Deg 1 both before and after surgery had significantly greater release of serum markers than patients who never had the product.

The quantity of modification associated with being in each of the tissue groups A through D was analysed to look for changes between before and after cross-clamp, and for differences between groups. Neither Groups A nor B experienced significant changes in the amount of modification products between before and after cross-clamp, while Group C patients saw significant decreases in the quantity of each product following cross-clamp removal. Patients in Group A for each product had the largest quantity of each product, followed by patients in Group C, Group B and Group D. This suggests that patients who have degradation products both before and after surgery (Group A) have greater quantities of modified products, but experience little change. However, patients who have degradation products before but not after surgery (Group C) experience a significant change with surgery, likely resulting from the release of cTnI modification products from the myocardium into the serum over the course of the surgery.

E. Relationship between cTnI Modification and Clinical Variables

Figure 9:
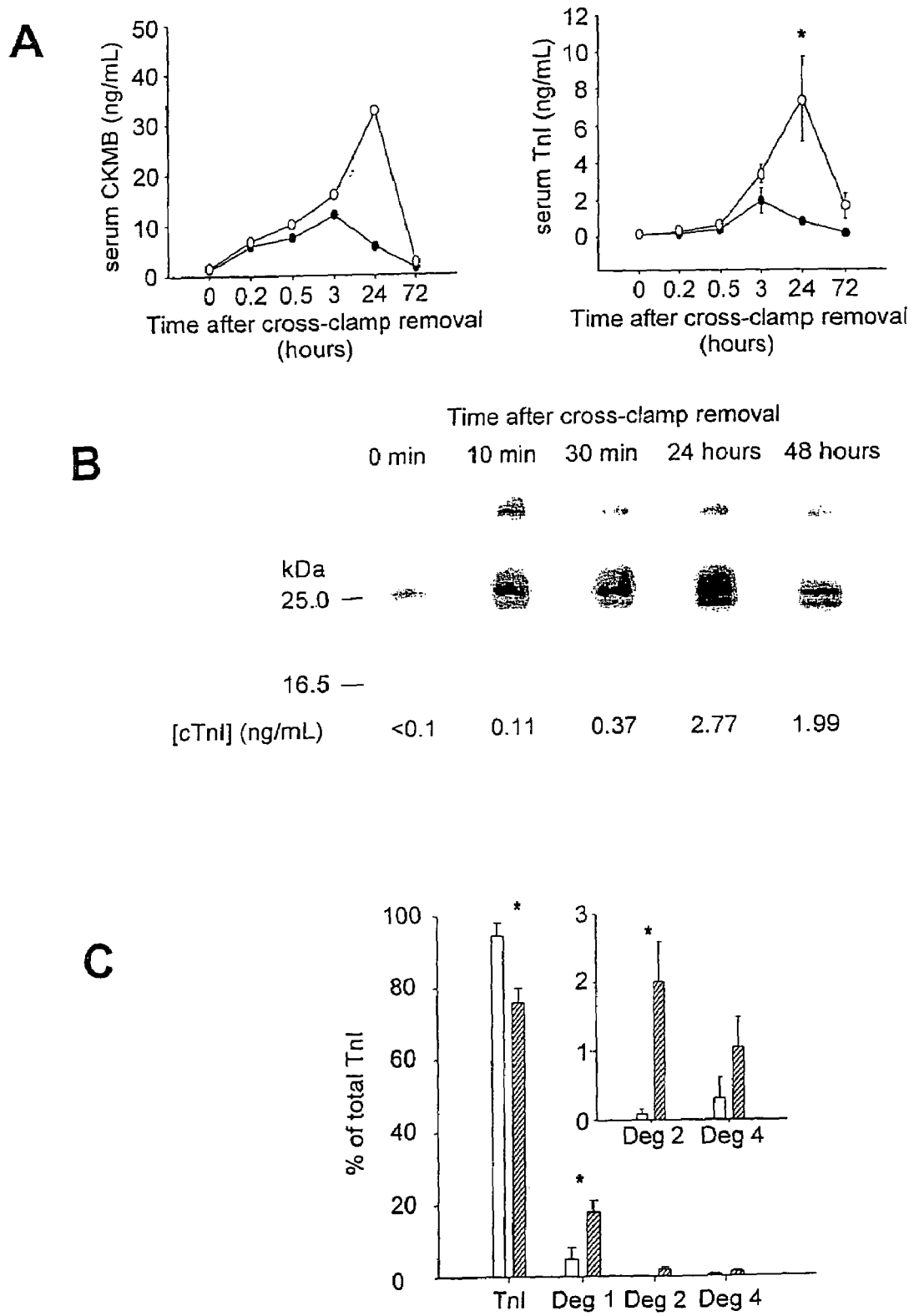
FIG. 9 shows stratification of patients according to CKMB release profile. Patients were assigned to one of two groups based on their serum CKMB levels 24 hours following cross-clamp removal (see Table 2).

To investigate whether the cTnI modification observed in myocardium could be linked to clinical variables, including the serum CKMB groups established in FIG. 9, both the tissue groups (Groups A, B, C, and D) and blood groups (Groups 1 and 2) were analyzed for significant relationships with pre-existing conditions and surgical times. The overall patient demographics are shown in Table 3. The surgical times and length of hospital stay for patients in the tissue and serum groups are compared in Table 4. Patients with either Deg 1, Deg 2, or Deg 4 both before and after cross-clamp (Group A), or elevated serum CKMB 24 hours following cross-clamp removal (Group 2), generally experienced longer total bypass times, longer cross-clamp times, and longer reperfusion times following removal of the cross-clamp. Patients with elevated CKMB 24 hours following cross-clamp removal also experienced longer hospital stays.

The presence of specific cTnI modification products in myocardium either before or after surgery was found to be associated with pre-existing medical conditions including a previous myocardial infarct, diabetes, and a history of class IV angina (Table 5). While these associations are statistically significant, none of the individual products is both highly selective and highly specific for any given condition. This is not surprising given the small sample size, and strongly suggests the importance of a large scale study to fully investigate the role of pre-existing medical conditions and disease states on the processes that result in cTnI modification.

Finally, each tissue group (A, B, C, D) was examined to determine if there was a relationship with the serum groups (1 and 2). Patients who were in Group A and D, with respect to Deg 1, were also found to be in Groups 2 and 1 respectively in the serum analysis (Table 6). The same is true for patients in groups A and D with respect to Deg 2. This suggests that the tissue profiles of cTnI modification are related to the release of serum markers.

EXAMPLE IV

Modification of TnT and TnC in Swine During Ischemia-Induced HF

Methods

Neutered male pigs (15-20 kg) underwent open chest surgery for occlusion of the anterior descending branch of left coronary artery (LAD) under general anaesthesia (isofluorone). Sham-operated animals underwent the same surgical procedure except the LAD was not occluded. 30 min post-ligation the chest was closed. Any episodes of ventricular fibrillation during the 30 min were terminated by external direct current countershocks. The animals were allowed to recover and received routine postoperative care. Survival rate for the LAD-ligation surgery was 87%. Echocardiography was performed on conscious animals 4 weeks post-operation. Animals were sacrificed under general anaesthesia 6 weeks post-operation The hearts were excised and trabeculae isolated from left ventricle were placed in ice-cold 50% (v/v) glycerol and relaxing buffer, protease inhibitor cocktail and 10 mM BDM for storage for skinned fiber bundles experiments (not described here). The remaining left ventricle tissue was immediately sectioned within infarcted (I) as well as non-infarcted (NI) areas and snap-frozen in liquid nitrogen.

2-D Gel Electrophoresis

The first dimension separation of proteins, from whole tissue homogenates, was performed either in IPG strips or slab IEF gels. IPG strips pH 4-7 and pH 7-10 (linear gradient) (Protean IEF cell, Bio-Rad) were rehydrated in the presence of protein sample in rehydration buffer (8M urea, 2% (w/v) CHAPS, 0.5% Bio-Lyte 3/10 Ampholyte, 15 mM DTT, 1% bromphenol blue) at 50 V for 12 h. Focusing was conducted for a total of 25000 Vh. 5.1% polyacrylamide slab QEF gels were prepared using different combination of narrow and broad range ampholytes (Bio-Rad) and focused at 400 V for 5 h.

The second dimension separation for both types of first dimension gels was performed in 12 or 15% resolving, 4.5% stacking gel by SDS-PAGE. The proteins from the gels were either silver stained or transferred to nitrocellulose membrane for immunoblot analysis with various anti-TnI monoclonal antibody or anti-TnT antibody.

Results

Figure 11:
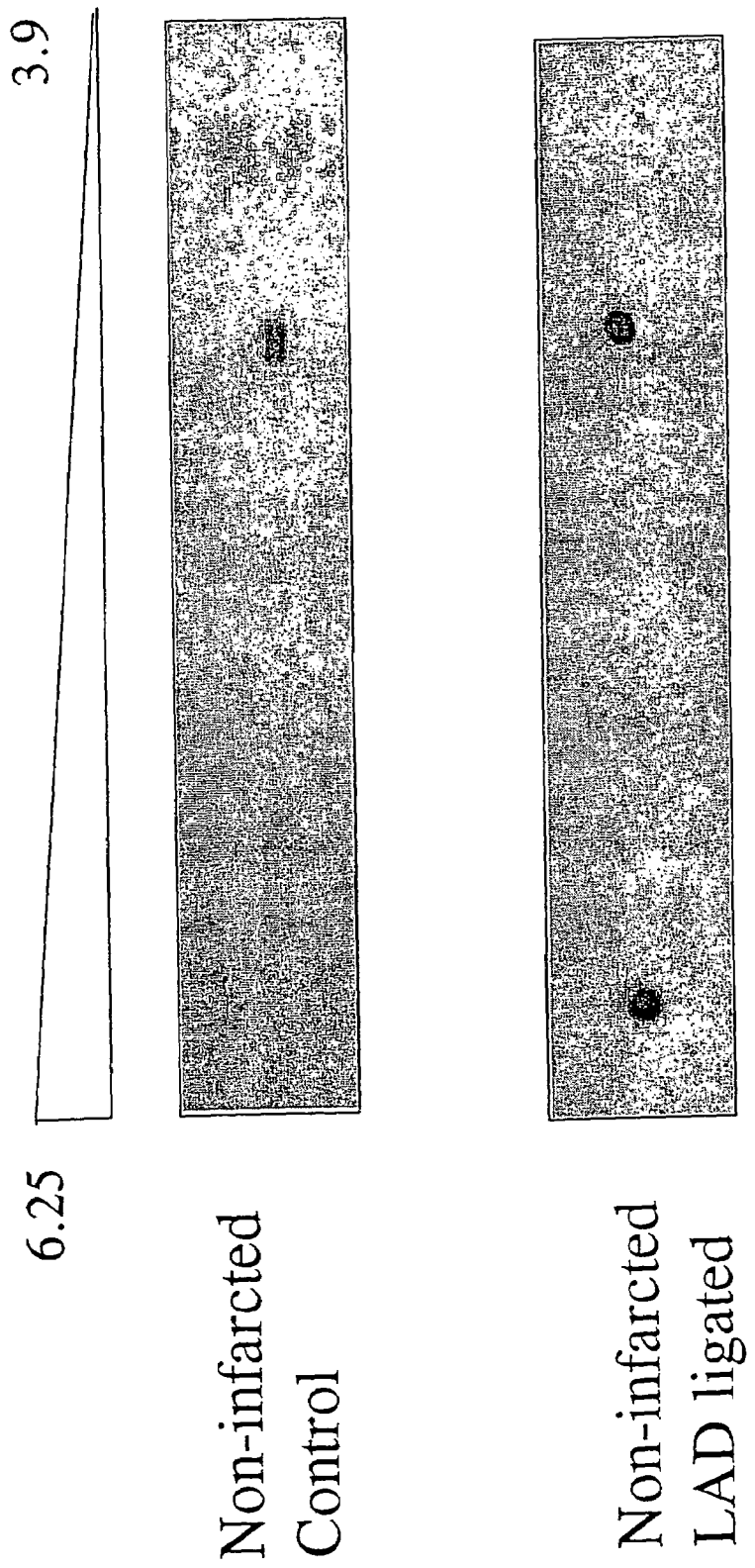
FIG. 11 shows a 2-D gel (and western blot of control) of the non-infarcted region of swine heart following ischemia-induced HF.

FIG. 11 shows a 2-D gel (and western blot of control) of the non-infarcted region of swine heart following ischemia-induced HF. The results indicate that post-translational modification of TnT causes a large increase in pI, from 4.5 to about 6.0, which suggests that the modification is glycosylation.

Figure 12:
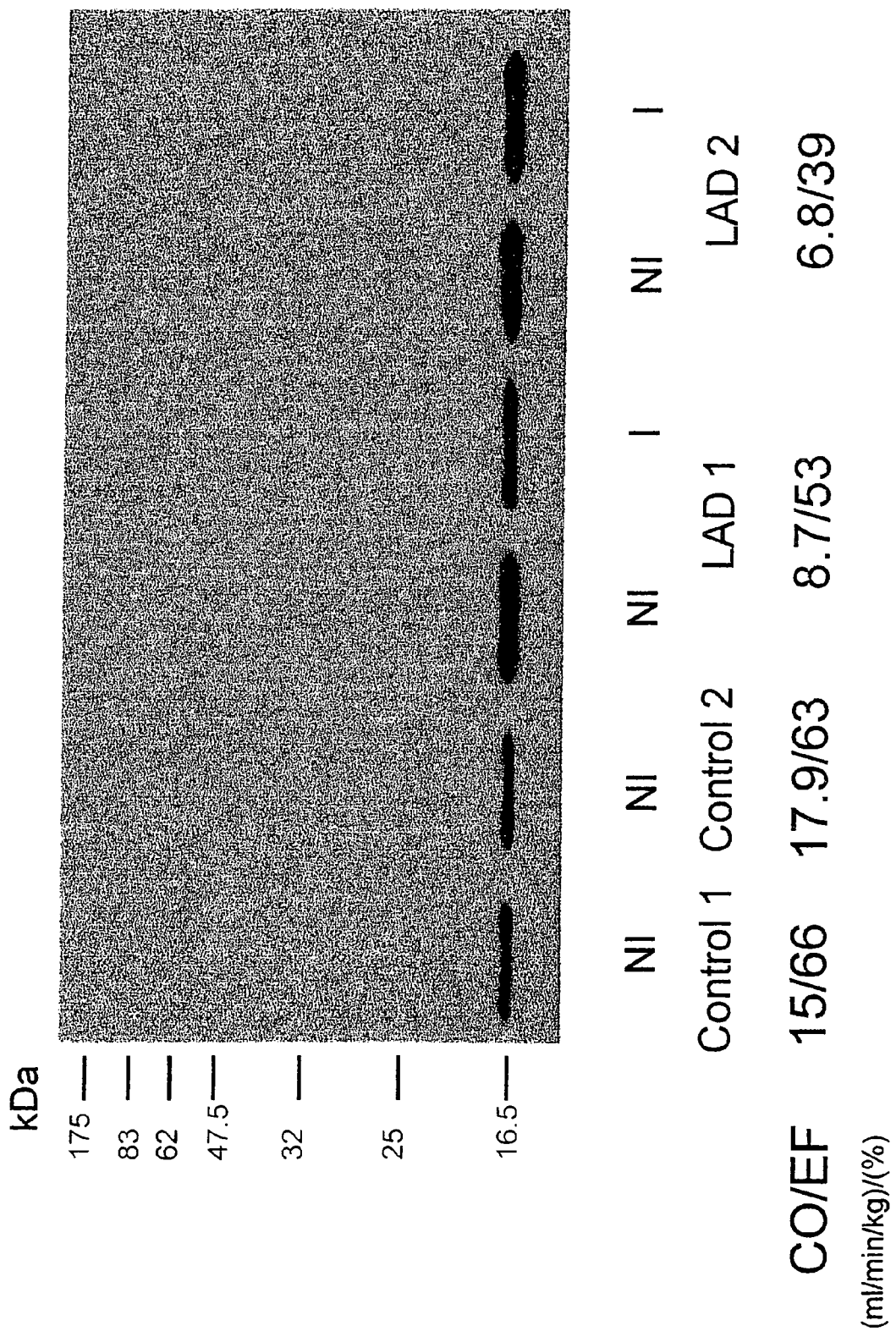
FIG. 12 shows the results of a western blot on TnC from control and LAD-occluded swine hearts.

FIG. 12 shows the results of a western blot on TnC from control and LAD-occluded swine hearts. As can be seen from the figure, increased expression of TnC is correlated with decreased cardiac function.

EXAMPLE V

Myofilament Protein Modification Products in Human Myocardium

Methods

Tissue samples were obtained from rejected human hearts following unsuccessful transplant attempts. Tissues were prepared and western blots were performed as described in Example III, and 2-D gels were performed as described in Examples II and IV, using anti-TnI antibodies 8I-7 and 2I-14.

Results

Figure 13:
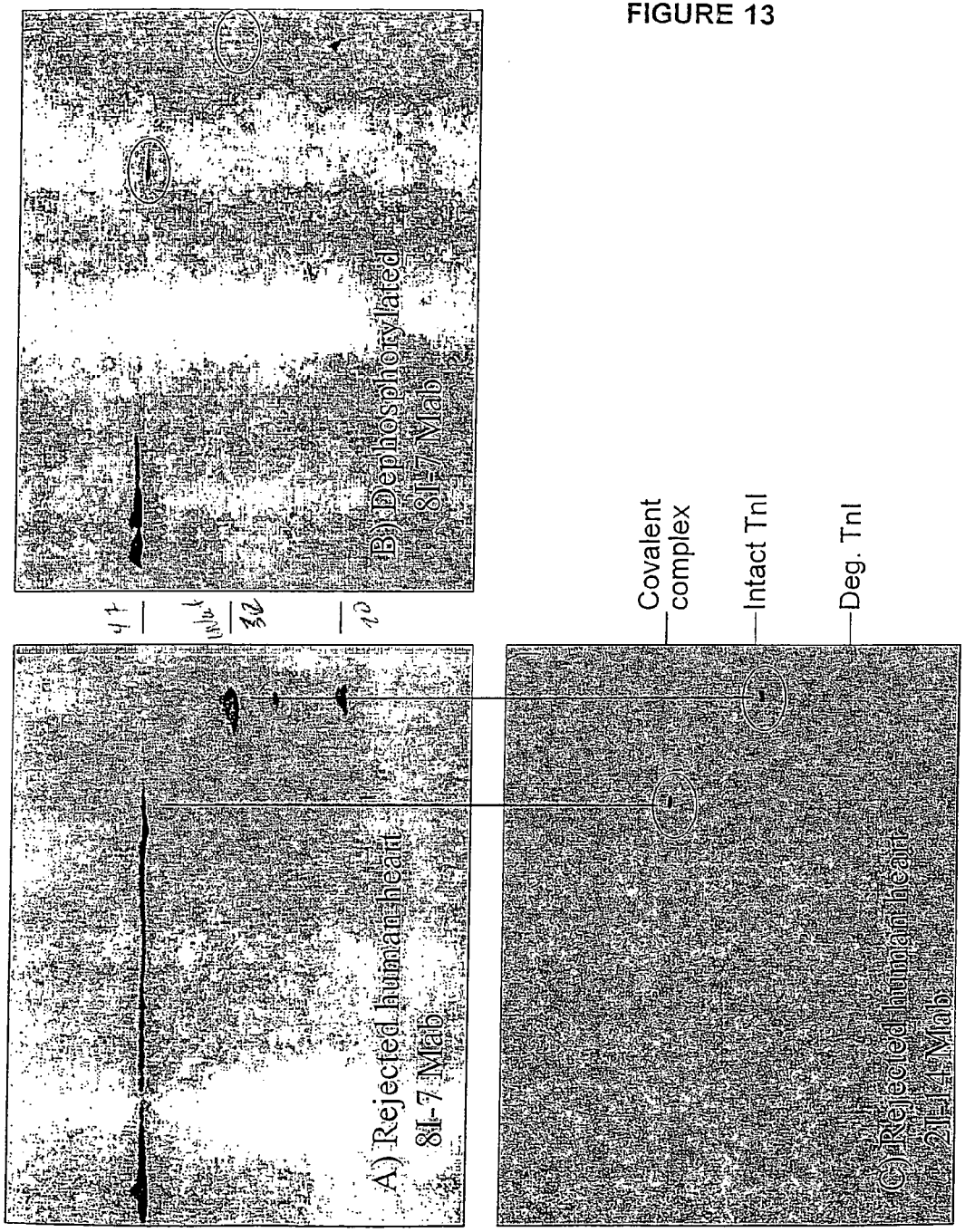
FIG. 13A shows intact TnI and degradation products and protein-protein complexes thereof detected in rejected human hearts.
FIG. 13B shows that dephosphotylation with alkaline phosphatase indicated extensive phosphorylation of protein-protein complexes involving TnI in rejected human hearts.
FIG. 13C shows a gel which confirms the presence of dephosphorylated forms of intact TnI and protein-protein complexes involving TnI.
Figure 14:
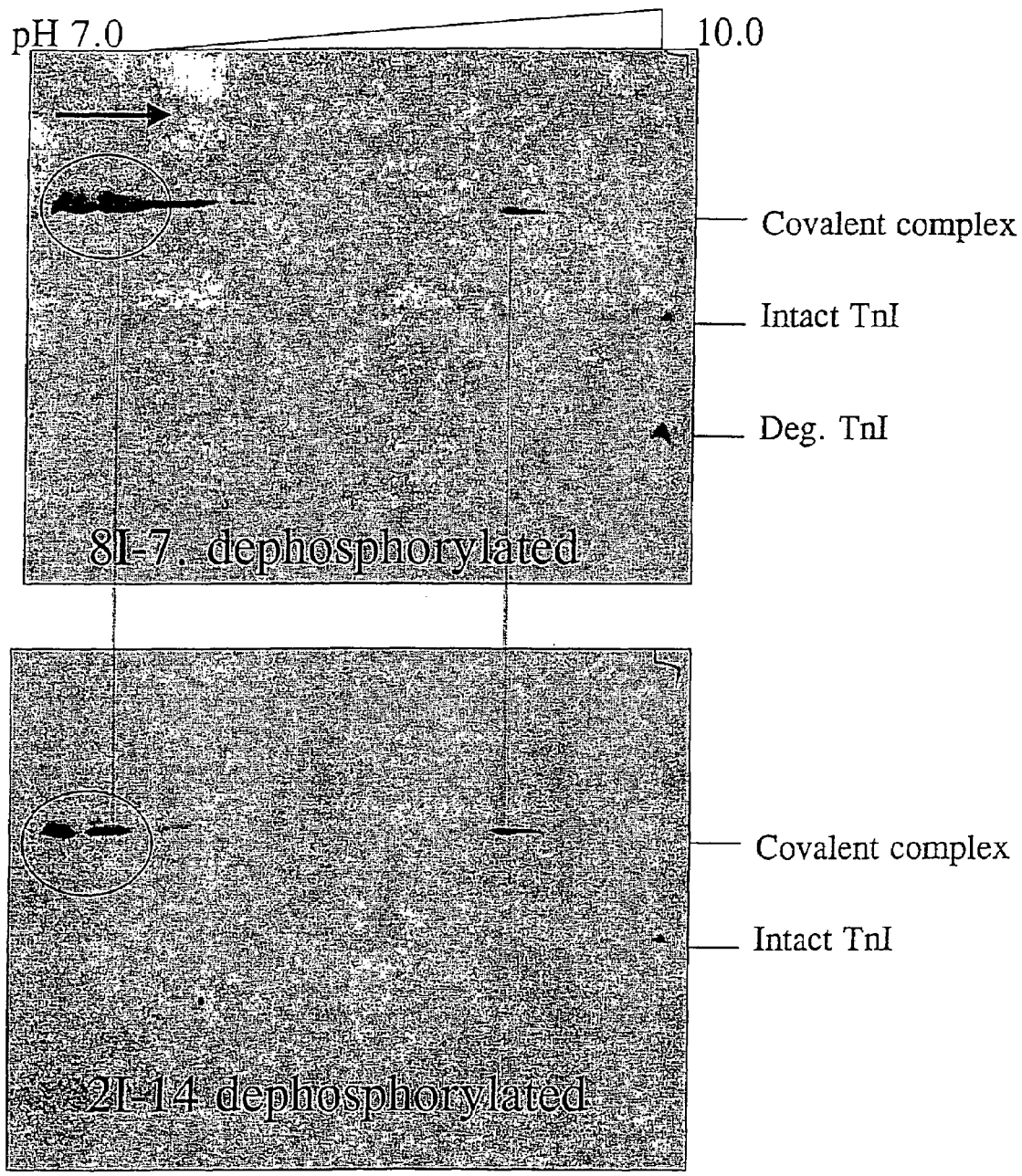
FIGS. 14A and B are gels showing that two distinct dephosphorylated forms of protein-protein complexes are present in human heart.

As shown in FIG. 13A, using the 8I-7 antibody, intact TnI as well as degradation products and protein-protein complexes were detected in the rejected human heart Dephosphorylation with alkaline phosphatase indicated extensive phosphorylation of protein-protein complexes involving TnI (FIG. 13B). The presence of dephosphorylated forms of intact TnI and protein-protein complexes involving TnI was confirmed in the gel shown in FIG. 13C, and two distinct dephosphorylated forms of protein-protein complexes can be seen in the gels of FIGS. 14A and B. Taken together, these results indicate that intact TnI and unphosphorylated forms of protein-protein complexes involving TnI are among the first modification products formed during HF. Further analysis revealed that there are at least seven phosphorylation sites, with a unique and possibly novel phosphorylation that occurs at residue 122, 128 or 142. Such phosphorylation does not occur with the intact protein. As well, TnI covalent complex is present in large amounts relative to acute situations.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 1

Identification of proteins affected by ischemia and ischemia/reperfusion by amino acid sequencing

| Amino Acid Sequence | Protein | Residue Number | First Identified Amino Acid (pmole) | Tissue Sampled |
|---|---|---|---|---|
| XXKKPE(P/A)KADDA (SEQ ID NO:1) | myosin light chain1 | 1-12 | 2.6 | global ischemia myofibrils & 60I/45RP tissue |
| XPAPAAAPAAAP (SEQ ID NO:2) | myosin light chain1 | 20-31 | 6.0 | global ischemia myofibrils |
| XKVALGAXGGI (SEQ ID NO:3) | malate dehydrogenase | 1-11 | 3.2 | 60I/45 RP tissue |
| XXLKDITRRLKSI (SEQ ID NO:4) | ATP g synthase chain | 1-13 | 4.5 | 60I/45RP tissue |
| XXKLVRPPVQ (SEQ ID NO:5) | ATP synthase oligomycin conferring protein | 1-10 | 2.3 | 60I/45RP tissue |
| XAHKSEIAHR (SEQ ID NO:6) | serum albumin | 1-10 | 12.4 | 60I/45RP effluent |
| XPS(R/L)KFFVGGN (SEQ ID NO:7) | triose phosphate isomerase | 1-11 | 9.9 | 60I/45RP effluent |

TABLE 2

Comparison of coronary artery bypass patients based on their serum CKMB release profiles and profiles of cTnI modification in myocardium was facilitated using the groups described.

| Source | Group | Criteria |
|---|---|---|
| Serum | Group 1 | Patients with serum CKMB < 8 ng/mL 24 hours following removal of the aortic cross-clamp |
| | Group 2 | Patients with serum CKMB > 8 ng/mL 24 hours following removal of the aortic cross-clamp |
| Tissue | Group A | Patients with specific modification product present both before and after surgery |
| | Group B | Patients with specific modification product that is not present before, but is present after, surgery |
| | Group C | Patients with specific modification product that is present before, but not present after, surgery |
| | Group D | Patients with specific modification product never present, either before or after surgery |

TABLE 3

Demographics of patients who underwent elective coronary artery bypass surgery. Post-operative complications, including atrial fibrillation, ventricular fibrillation, wound infection, and post-pMI were in this category.

| | | |
|---|---|---|
| Total Patients: n (%) | 37 | (100.0) |
| Surgical Variables | | |
| Total minutes on bypass: mean (SD) | 98 | (19) |
| Total minutes on cross-clamp: mean (SD) | 72 | (17) |
| Total minutes of reperfusion: mean (SD) | 22 | (5) |
| No. grafts: median (range) | 4 | (3-7) |
| Pacing used: n (%) | 6 | (16.2) |
| Inotropes used: n (%) | 6 | (16.2) |
| Pre-existing Conditions | | |
| Age: mean (SD) | 63 | (8) |
| Male sex: n (%) | 33 | (89.2) |
| Hypertension: n (%) | 15 | (40.5) |
| Hyperlipidemia: n (%) | 23 | (62.2) |
| Family history of cardiac illness: n (%) | 28 | (75.7) |
| Previous MI: n (%) | 24 | (64.9) |
| Recent MI (last 12 months): n (%) | 13 | (35.2) |
| Diabetes: n (%) | 11 | (29.7) |
| Chronic Obstructive Pulmonary Disease: n (%) | 9 | (24.3) |
| Daily smoker within the last 10 years: n (%) | 29 | (78.4) |
| Positive stress test: n (%) | 23 | (62.2) |
| LV Function Grade III or IV: n (%) | 9 | (24.3) |
| Pre-surgery LV ejection fraction: median % (inter-quartile range) | 50 | (35, 60) |

TABLE 5

Data showing that the presence of specific TnI modification products in LV tissue before and after cross-clamping is associated with specific pre-existing conditions.

| Pre-existing disease | Product | Timing (before/after cross-clamp) | Correct prediction of pre-existing disease state — Condition Present | Condition Absent | Missing Data (n) | Exact p-value |
|---|---|---|---|---|---|---|
| Recent MI (last 12 months) | Deg 2 | after | 9/11 | 16/22 | 4 | 0.008 |
| Previous MI | Deg 2 | before | 12/20 | 9/12 | 5 | 0.076 |
| Class IV Angina | Deg 4 | before | 10/17 | 9/10 | 10 | 0.018 |
| Diabetes | Deg 2 | after | 8/10 | 16/24 | 3 | 0.023 |

TABLE 4

Differences in cTnI modification profiles and CKMB release profiles with respect to length of surgery and hospital stay. In panel A, * indicates significantly different time than tissue group A, and † indicates significantly different time than tissue group B ($p < 0.05$). In panel B, significant differences between the two serum groups, 1 and 2, are given as * $p < 0.10$, and ** $p < 0.05$.

A

| Degradation Product | Surgical Times (min) | Group A n | mean | SD | Group B n | mean | SD | Group C n | mean | SD | Group D n | mean | SD |
|---|---|---|---|---|---|---|---|---|---|---|---|---|---|
| Deg 1 | Bypass | 20 | 105 | 16 | 3 | 90 | 25 | 3 | 77* | 9 | 5 | 89 | 30 |
| | Cross-Clamp | 20 | 76 | 13 | 3 | 67 | 22 | 3 | 54* | 10 | 5 | 67 | 28 |
| | Reperfusion | 20 | 23 | 6 | 3 | 20 | 5 | 3 | 19 | 2 | 5 | 18 | 3 |
| Deg 2 | Bypass | 13 | 100 | 19 | 2 | n/a | n/a | 3 | 90 | 9 | 13 | 97 | 25 |
| | Cross-Clamp | 13 | 72 | 15 | 2 | n/a | n/a | 3 | 66 | 9 | 13 | 72 | 23 |
| | Reperfusion | 13 | 24 | 5 | 2 | n/a | n/a | 3 | 22 | 3 | 13 | 19* | 4 |
| Deg 4 | Bypass | 9 | 107 | 18 | 3 | 98 | 4 | 5 | 88* | 15 | 14 | 96 | 24 |
| | Cross-Clamp | 9 | 77 | 14 | 3 | 68 | 4 | 5 | 67 | 16 | 14 | 71 | 22 |
| | Reperfusion | 9 | 25 | 6 | 3 | 27 | 2 | 5 | 19*† | 2 | 14 | 20*† | 4 |

B

| | Total Bypass Time (min) n | mean | SD | Total Cross-Clamp Time (min) n | mean | SD | Total Reperfusion Time (min) n | mean | SD | Length of Hospital Stay (days) n | mean | SD |
|---|---|---|---|---|---|---|---|---|---|---|---|---|
| Group 1 | 8 | 86 | 23 | 8 | 64 | 23 | 8 | 19 | 2 | 8 | 5.0 | 0.8 |
| Group 2 | 25 | 100* | 17 | 25 | 72 | 14 | 25 | 23** | 5 | 24 | 8.3** | 6.4 |

TABLE 6

Data showing that the presence of Deg 1 or Deg 2 both before and after surgery is associated with elevated serum CKMB 24 hours following surgery. Patients who had either Deg 1 or Deg 2 both before and after surgery were also found to be in serum group 2 (with elevated 24 hour serum CKMB), while patients who never had the degradation products were found to be in group 1 (without elevated 24 hour serum CKMB). This is reinforced by the serum release profiles demonstrated in FIGS. 9A and 10B.

| Degradation Product | Presence of Degradation Product (Tissue Group) | Correct Prediction of Serum Group | | Exact p-value |
|---|---|---|---|---|
| | | 1 | 2 | |
| Deg 1 | n | 4 | 18 | 0.024 |
| | Both before and after (A) | 1 | 16 | |
| | Never present (D) | 3 | 2 | |
| Deg 2 | n | 5 | 17 | 0.040 |
| | Both before and after (A) | 0 | 10 | |
| | Never present (D) | 5 | 7 | |

We claim:

1. A method for assessing skeletal muscle damage in a subject, comprising:
   obtaining a biological sample from a subject being assessed for skeletal muscle damage; and
   evaluating for the presence of one or more different myofilament protein modification products in the biological sample, at least one of said myofilament protein modification products being a chemical adduct of a myofilament protein selected from the group consisting of skeletal troponin I, skeletal troponin T and myosin light chain 1;
      wherein the presence of at least one myofilament protein modification product which is a chemical adduct of a myofilament protein selected from the group consisting of skeletal troponin I, skeletal troponin T and myosin light chain 1 in the biological sample is indicative of skeletal muscle damage in said subject; and
   wherein the chemical adduct of the myofilament protein is a post-translational modification of an intact myofilament protein, a post-translational modification of a degradation product of a myofilament protein or a post-translational modification of a protein-protein complex of myofilament proteins and said myofilament protein is selected from the group consisting of skeletal troponin I, skeletal troponin T and myosin light chain 1.

2. The method of claim 1,
   further comprising the step of assessing the amount of the one or more different myofilament protein modification products present in the biological sample as an indication of the extent of skeletal muscle damage in the subject, wherein at least one of said myofilament protein modification products is a chemical adduct of a myofilament protein selected from the group consisting of skeletal troponin I, skeletal troponin T and myosin light chain 1.

3. The method of claim 1, wherein the evaluating step comprises detecting the presence of at least two different myofilament protein modification products in the biological sample, wherein at least one of said myofilament protein modification products is a chemical adduct of a myofilament protein selected from the group consisting of skeletal troponin I, skeletal troponin T and myosin light chain 1.

4. The method of claim 3, further comprising the step of assessing the amounts of said at least two different myofilament protein modification products present in the biological sample, and comparing the amounts as an indication of the extent of skeletal muscle damage in the subject, wherein at least one of said myofilament protein modification products is a chemical adduct of a myofilament protein selected from the group consisting of skeletal troponin I, skeletal troponin T and myosin light chain 1.

5. The method of claim 3, wherein said at least two different myofilament protein modification products are from the same protein, wherein at least one of said myofilament protein modification products is a chemical adduct of a myofilament protein selected from the group consisting of skeletal troponin I, skeletal troponin T and myosin light chain 1.

6. The method of claim 3, wherein said at least two different myofilament protein modification products are from different proteins, wherein at least one of said myofilament protein modification products is a chemical adduct of a myofilament protein selected from the group consisting of skeletal troponin I, skeletal troponin T and myosin light chain 1.

7. The method of claim 6, further comprising the step of assessing the ratio of said at least two different myofilament protein modification products as an indication of the extent of skeletal muscle damage in the subject, wherein at least one of said myofilament protein modification products is a chemical adduct of a myofilament protein selected from the group consisting of skeletal troponin I, skeletal troponin T and myosin light chain 1.

8. The method of claim 1, wherein the skeletal muscle damage is due to at least one condition selected from the group consisting of hypoxia, hypoxemia, ischemia, and reperfusion.

9. The method of claim 8, wherein the skeletal muscle damage is reversible.

10. The method of claim 8, wherein the skeletal muscle damage is irreversible.

11. The method of claim 1, wherein at least one of the myofilament protein modification products is a protein-protein complex comprising at least two polypeptides, at least one of said polypeptides being a chemical adduct of an intact protein or a fragment of a protein selected from the group consisting of skeletal troponin I, skeletal troponin T and myosin light chain 1.

12. The method of claim 1, wherein at least one of the myofilament protein modification products is a chemical adduct of a degradation product of a myofilament protein selected from the group consisting of skeletal troponin I, skeletal troponin T and myosin light chain 1.

13. The method of claim 1, wherein the chemical adduct of a myofilament protein is a myofilament protein modified by post-translational modification.

14. The method of claim 13, wherein the post-translational modification is selected from the group consisting of phosphorylation, glycosylation, myristylation, phenylation, acetylation, nitrosylation, and sulphation.

15. The method of claim 11, wherein the chemical adduct of a myofilament protein is a protein-protein complex modified by post-translational modification.

16. The method of claim 15, wherein the post-translational modification is selected from the group consisting of phosphorylation, glycosylation, myristylation, phenylation, acetylation, nitrosylation, and sulphation.

17. The method of claim 12, wherein the chemical adduct of a myofilament protein is a degradation product of a myofilament protein modified by post-translational modification.

18. The method of claim 17, wherein the post-translational modification is selected from the group consisting of phosphorylation, glycosylation, myristylation, phenylation, acetylation, nitrosylation, and sulphation.

19. The method of claim 1, wherein the myofilament protein is myosin light chain 1.

20. The method of claim 1, wherein the biological sample is selected from the group consisting of blood, blood serum, blood plasma, skeletal muscle tissue, a component of skeletal muscle tissue, and urine.

21. A method for assessing skeletal muscle damage in a subject, comprising:
   obtaining at least two biological samples from a subject being assessed for skeletal muscle damage; and
   evaluating for the presence of one or more myofilament protein modification products in the biological samples;
   wherein said biological samples are not obtained simultaneously;
   wherein at least one of the myofilament protein modification products is a chemical adduct of a myofilament protein selected from the group consisting of skeletal troponin I, skeletal troponin T and myosin light chain 1;
   wherein the presence of one or more chemical adducts of a myofilament protein selected from the group consisting of skeletal troponin I, skeletal troponin T and myosin light chain 1 in at least one of said biological samples is indicative of skeletal muscle damage in the subject; and wherein the chemical adduct of the myofilament protein selected from the group consisting of skeletal troponin I, skeletal troponin T and myosin light chain 1 is a post-translational modification of an intact myofilament protein, a post-translational modification of a degradation product of a myofilament protein or a post-translational modification of a protein-protein complex of myofilament proteins.

22. The method of claim 21, further comprising assessing a change with time in the presence or amount of one or more chemical adducts of a myofilament protein selected from the group consisting of skeletal troponin I, skeletal troponin T and myosin light chain 1 in the biological samples, as an indication of the extent of skeletal muscle damage in the subject.

23. The method of claim 21, wherein the evaluating step comprises detecting the presence of at least two different chemical adducts of a myofilament protein in the biological samples.

24. The method of claim 23, further comprising the step of assessing a change with time in the amounts of said at least two different chemical adducts of a myofilament protein present in the biological samples, as an indication of the extent of skeletal muscle damage in the subject.

25. The method of claim 23, wherein said at least two different chemical adducts of a myofilament protein are from the same protein.

26. The method of claim 23, wherein said at least two different chemical adducts of a myofilament protein are from different proteins.

* * * * *

SEQUENCE LISTING

<160> NUMBER OF SEQ ID NOS: 7

<210> SEQ ID NO 1
<211> LENGTH: 12
<212> TYPE: PRT
<213> ORGANISM: Rattus sp.
<220> FEATURE:
<221> NAME/KEY: UNSURE
<222> LOCATION: (1)..(2)
<223> OTHER INFORMATION: any amino acid
<220> FEATURE:
<221> NAME/KEY: UNSURE
<222> LOCATION: (7)
<223> OTHER INFORMATION: P or A

<400> SEQUENCE: 1

Xaa Xaa Lys Lys Pro Glu Xaa Lys Ala Asp Asp Ala
 1               5                  10

<210> SEQ ID NO 2
<211> LENGTH: 12
<212> TYPE: PRT
<213> ORGANISM: Rattus sp.
<220> FEATURE:
<221> NAME/KEY: UNSURE
<222> LOCATION: (1)
<223> OTHER INFORMATION: any amino acid

<400> SEQUENCE: 2

Xaa Pro Ala Pro Ala Ala Ala Pro Ala Ala Ala Pro
 1               5                  10

<210> SEQ ID NO 3
<211> LENGTH: 11
<212> TYPE: PRT
<213> ORGANISM: Rattus sp.
<220> FEATURE:
<221> NAME/KEY: UNSURE
<222> LOCATION: (1)
<223> OTHER INFORMATION: any amino acid
<220> FEATURE:
<221> NAME/KEY: UNSURE

```
<222> LOCATION: (8)
<223> OTHER INFORMATION: any amino acid

<400> SEQUENCE: 3

Xaa Lys Val Ala Leu Gly Ala Xaa Gly Gly Ile
 1               5                  10

<210> SEQ ID NO 4
<211> LENGTH: 13
<212> TYPE: PRT
<213> ORGANISM: Rattus sp.
<220> FEATURE:
<221> NAME/KEY: UNSURE
<222> LOCATION: (1)..(2)
<223> OTHER INFORMATION: any amino acid

<400> SEQUENCE: 4

Xaa Xaa Leu Lys Asp Ile Thr Arg Arg Leu Lys Ser Ile
 1               5                  10

<210> SEQ ID NO 5
<211> LENGTH: 10
<212> TYPE: PRT
<213> ORGANISM: Rattus sp.
<220> FEATURE:
<221> NAME/KEY: UNSURE
<222> LOCATION: (1)..(2)
<223> OTHER INFORMATION: any amino acid

<400> SEQUENCE: 5

Xaa Xaa Lys Leu Val Arg Pro Pro Val Gln
 1               5                  10

<210> SEQ ID NO 6
<211> LENGTH: 10
<212> TYPE: PRT
<213> ORGANISM: Rattus sp.
<220> FEATURE:
<221> NAME/KEY: UNSURE
<222> LOCATION: (1)
<223> OTHER INFORMATION: any amino acid

<400> SEQUENCE: 6

Xaa Ala His Lys Ser Glu Ile Ala His Arg
 1               5                  10

<210> SEQ ID NO 7
<211> LENGTH: 11
<212> TYPE: PRT
<213> ORGANISM: Rattus sp.
<220> FEATURE:
<221> NAME/KEY: UNSURE
<222> LOCATION: (1)
<223> OTHER INFORMATION: any amino acid
<220> FEATURE:
<221> NAME/KEY: UNSURE
<222> LOCATION: (4)
<223> OTHER INFORMATION: R or L

<400> SEQUENCE: 7

Xaa Pro Ser Xaa Lys Phe Phe Val Gly Gly Asn
 1               5                  10
```